(12) United States Patent
Benner et al.

(10) Patent No.: US 7,851,224 B2
(45) Date of Patent: Dec. 14, 2010

(54) METHOD OF ASSESSING A LIPID-RELATED HEALTH RISK BASED ON ION MOBILITY ANALYSIS OF LIPOPROTEINS

(75) Inventors: W. Henry Benner, Danville, CA (US);
Ronald M. Krauss, Berkeley, CA (US);
Patricia J. Blanche, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/775,225

(22) Filed: May 6, 2010

(65) Prior Publication Data

US 2010/0213061 A1 Aug. 26, 2010

Related U.S. Application Data

(62) Division of application No. 11/771,862, filed on Jun. 29, 2007, now Pat. No. 7,713,744, which is a division of application No. 10/293,610, filed on Nov. 12, 2002, now Pat. No. 7,259,018.

(60) Provisional application No. 60/338,214, filed on Nov. 13, 2001.

(51) Int. Cl.
*G01N 33/92* (2006.01)
*G01N 24/00* (2006.01)
(52) U.S. Cl. .................... 436/71; 436/173; 436/13
(58) Field of Classification Search .................. None
See application file for complete search history.

(56) References Cited

U.S. PATENT DOCUMENTS 4,933,844 A 6/1990 Otvos (Continued)

FOREIGN PATENT DOCUMENTS

EP 0546916 A1 6/1993

(Continued)

OTHER PUBLICATIONS

Bacher, G. et al., *Charge-reduced nano electrospray ionization combined with differential mobility analysis of peptides, proteins, glycoproteins, noncovalent protein complexes and viruses*, Journal of Mass Spectrometry, vol. 36 (No. 9), p. 1038-1052, Sep. 2001.

(Continued)

*Primary Examiner*—Yelena G Gakh
(74) *Attorney, Agent, or Firm*—Knobbe, Martens, Olson & Bear LLP

(57) ABSTRACT

A medical diagnostic method and instrumentation system for analyzing noncovalently bonded agglomerated biological particles is described. The method and system comprises: a method of preparation for the biological particles; an electrospray generator; an alpha particle radiation source; a differential mobility analyzer; a particle counter; and data acquisition and analysis means. The medical device is useful for the assessment of human diseases, such as cardiac disease risk and hyperlipidemia, by rapid quantitative analysis of lipoprotein fraction densities. Initially, purification procedures are described to reduce an initial blood sample to an analytical input to the instrument. The measured sizes from the analytical sample are correlated with densities, resulting in a spectrum of lipoprotein densities. The lipoprotein density distribution can then be used to characterize cardiac and other lipid-related health risks.

20 Claims, 15 Drawing Sheets

U.S. PATENT DOCUMENTS

| | | | |
|---|---|---|---|
| 5,076,097 | A | 12/1991 | Zarrin et al. |
| 5,247,842 | A | 9/1993 | Kaufman et al. |
| 5,343,389 | A | 8/1994 | Otvos |
| 5,788,166 | A | 8/1998 | Valaskovic et al. |
| 5,856,196 | A | 1/1999 | Alvarez et al. |
| 5,925,229 | A | 7/1999 | Krauss et al. |
| 6,145,391 | A | 11/2000 | Pui et al. |
| 6,248,545 | B1 | 6/2001 | Kondo et al. |
| 6,267,579 | B1 | 7/2001 | Li et al. |
| 6,485,686 | B1 | 11/2002 | Wick |
| 6,491,872 | B1 | 12/2002 | Wick |

FOREIGN PATENT DOCUMENTS

| | | |
|---|---|---|
| EP | 1045247 A2 | 10/2000 |
| JP | 2000-214150 | 4/2000 |
| WO | WO 99/17096 | 4/1999 |
| WO | WO 00/51054 | 8/2000 |
| WO | WO 00/65366 | 11/2000 |

OTHER PUBLICATIONS

Henderson et al., *Intrinsic Size Parameters for Val, Ile, Leu, Gln, Thr, Phe, and Trp Residues from Ion Mobility Measurements of Polyamino Acid Ions*, J. Phys. Chem. B, vol. 103, p. 8780-8785, 1999.

Benner et al. *Investigating Intact Viruses with Charge-Detection MS and Ion Mobility*, Proc. 49$^{th}$ ASMS Conf. on Mass Spectrometry and Allied Topics, ASMS, Chicago IL, May 27, 2001.

Bundy et al., *A novel Method for the Analysis of Complex Biological Protein Mixtures Using Electrospray Ionization Mass Spectrometry Combined with Ion/Ion Chemistry*, Proc. 49$^{th}$ ASMS Conf. on Mass Spectrometry and Allied Topics, ASMS, Chicago IL, May 27, 2001.

Krauss, Ronald M., *Triglyceride-Rich Lipoproteins, LDL Particle Size, and Atherogenesis*, American Assoc. of Clinical Endocrinologists Ninth Annual Meeting and Clinical Congress, Amer. Assoc. Cinical Endocrinologists, May 3, 2000.

Krauss et al., *Detection and quantitation of LDL subfractions*, Current Opinion in Lipidology, Current Science Ltd., vol. 3, p. 377-383, 1992.

TSI Incorporated, *Model 3080-Series Electrostatic Clasifiers*, TSI Product Info. Sheets (www. tsi.com), TSI Incorporated, USA, 1999.

Tsi Incorporated, *Model 3980 GEMMA Macromolecule Analyzer*, TSI Advance Product Information (www. tsi.com), TSI Incorporated, USA, 2000.

TSI Incorporated, *Model 3312 Ultraviolet Aerodynamic Particle Sizer Spectrometer*, Preliminary Product Information (www. tsi.com), TSI Incorporated, USA, 1997.

TSI Incorporated, *Correlation of EM Diameter with Molecular Weight*, GEMMA Example—EM Diameter vs. Molecular Weight (www.tsi.com), TSI Incorporated, Particle Instrumentation Division, USA, 1999.

TSI Incorporated, *GEMMA Method for Macromolecule/ Nanoparticle Analysis*, GEMMA Method Product Page (www.tsi.com), TSI Incorporated, Particle Instrument Division, USA, 1999.

TSI Incorporated, *Model 3480 Electrospray Aerosol Generator*, 3480 Advance Product Information (www. tsi.com), TSI Incorporated, Particle Instrument Division, USA, 1999.

New Objective, Inc., *Bring Electrospray Into Focus*, LC-MS Nano-ESI Proteomics, New Objective, Inc. (www.newobjective.com), USA, 2001.

Bell et al., [LJ.09] *The dynamics of a steady Taylor cone electrospray*, BAPSDFD98 Abstracts—Session LJ—Surface Tension Effects I., APS, USA, Aug. 1, 1998.

Bell et al., [LJ.09] *The dynamics of a steady Taylor cone electrospray*, BAPSDFD98 Abstracts—Session LJ—Surface Tension Effects I., APS, USA, Aug. 20, 2001.

Bell et al., [LJ.09] *The dynamics of a steady Taylor cone electrospray*, BAPSDFD98—Abstracts, American Physical Society, USA, Aug. 1, 1998.

New Objective, Inc., *What is Electrospray?*, Products (www. newobjective.com), New Objective, Inc., USA, 2001.

New Objective, Inc., *Product Catalog: Fused Silica Pico Tips*, Products (www.newobjective.com), New Objective, Inc., USA, 2001.

New Objective, Inc., *What New Objective Can Do for You*, www. newobjective.com, New Objective, Inc., Cambridge, MA.

TSI Incorporated, *Protein Mixture*, GEMMA Example—Protein Mixture (www. tsi.com), TSI Incorporated, Particle Instrument Division, USA, 1999.

Edmonds et al., *Capillary Electrophoresis-Electrospray Ionization-Mass Spectrometry*, J. Chromatogr., PNL, USA, p. 21-37, 1989.

Atherotech, Inc., *Test Benefits—VAP/CAD Lipoprotein Risk Assessment Test*, http://home.socal.rr.com/asylem/test_ben.htm, Artherotech, Inc., USA, p. 1-3, 2001.

Muniz et al., *A New Tool for the Automated Analysis of LDL Subfraction Patterns Generated by the Lipoprint LDL System*, www.4qc.com, Quantimetrix Corporation, USA, p. 1-11, 2001.

Quantimetrix Corporation, *Lipoprint System for LDL Subfraction*, Lipoprint Technical—What's New (www.4qc.com), Quantimetrix Corporation, USA, p. 1, 2001.

Quantimetrix Corporation, *Lipoprint System for LDL Subfraction Literature*, Lipoprint Literature (www.4qc.com), Quantimetrix Corporation, USA, p. 1-2, 2001.

Jeyarajah et al., *Radio signals give new spectrum for cholesterol lipoprotein readings*, American Heart Association Journal Report—News Release, American Heart Association, USA, p. 1-3, Jul. 9, 1998.

Hodis et al., *Intermediate-density lipoproteins and progression of carotid arterial wall intima-media thickness*, Circulation, vol. 95 (No. 8), p. 2022-2026, Apr. 15, 1997.

Dreon et al., *LDL subclass patterns and lipoprotein response to a low-fat, high-carbohydrate diet in women*, Arteriosclerosis, Thrombosis & Vascular Biology, vol. 17 (No. 4), p. 707-714, Apr. 1997.

Williams et al., *Variability of plasma HDL subclass concentrations in men and women over time*, Arteriosclerosis, Thrombosis & Vascular Biology, vol. 17 (No. 4), p. 702-706, Apr. 1997.

Mack et al., *Lipoprotein subclasses in the Monitored Atherosclerosis Regression Study (MARS). Treatment effects and relation to coronary angiographic progression*, Arteriosclerosis, Thrombosis & Vascular Biology, vol. 16 (No. 5), p. 697-704, 1996.

Stampfer et al., *A prospective study of triglyceride level, low-density lipoprotein particle diameter, and risk of myocardial infarction*, Comment in: JAMA, vol. 276 (No. 11), p. 882-888, Sep. 18, 1996.

Gardner et al., *Association of small low-density lipoprotein particles with the incidence of coronary artery disease in men and women*, Comment in: JAMA, vol. 276 (No. 11), p. 875-881, Sep. 18, 1996.

Campos et al., *Predominance of large LDL and reduced HDL2 cholesterol in normolipidemic men with coronary artery disease*, Arteriosclerosis, Thrombosis & Vascular Biology, vol. 15 (No. 8), p. 1043-1048, Aug. 1995.

Krauss et al., *Low-density-lipoprotein subclasses and response to a low-fat diet in healthy men*, American Journal of Clinical Nutrition, vol. 62 (No. 2), p. 478S-487S, Aug. 1995.

Williams et al., *Effects of dietary fat on high-density-lipoprotein subclasses are influenced by both apolipoprotein E isoforms and low-density-lipoprotein subclass patterns*, American Journal of Clinical Nutrition, vol. 61 (No. 6), p. 1234-1240, Jun. 1995.

Katzel, L.I. et al., *Persistence of low HDL-C levels after weight reduction in older men with small LDL particles*, Arteriosclerosis, Thrombosis & Vascular Biology, vol. 15 (No. 3), p. 299-305, Mar. 1995.

Williams, P.T. et al., *The associations of high-density lipoprotein subclasses with insulin and glucose levels, physical activity, resting heart rate, and regional adiposity in men with coronary artery disease. . .* , Metabolism: Clinical & Experimental, vol. 44 (No. 1), p. 106-114, Jan. 1995.

Haskell, W.L. et al., *Effects of intensive multiple risk factor reduction on coronary atherosclerosis and clinical cardiac events in men and women with coronary artery disease. The Stanford Coronary Risk Intervention Project (SCRIP)*, Circulation, vol. 89 (No. 3), p. 975-990, Mar. 1994.

Dreon, D.M. et al., *Low-density lipoprotein subclass patterns and lipoprotein response to a reduced-fat diet in men*, FASEB Journal, vol. 8 (No. 1), p. 121-126, Jan. 1994.

Superko, H.R. et al., *Association of lipoprotein subclass distribution with use of selective and non-selective beta-blocker medications in patients with coronary heart disease*, Atherosclerosis, vol. 101 (No. 1), p. 1-8, Jun. 1993.

Krauss, R.M. et al., *Lipoprotein subclasses in genetic studies: the Berkeley data set*, Genetic Epidemiology, vol. 10 (No. 6), p. 523-528, 1993.

Feingold, K.R. et al., *The hypertriglyceridemia of acquired immunodeficiency syndrome is associated with an increased prevalence of low density lipoprotein subclass pattern B*, Journal of Clinical Endocrinology & Metabolism, vol. 76 (No. 6), p. 1423-1427, Jun. 1993.

Williams, P.T. et al., *Associations of age, adiposity, alcohol intake, menstrual status, and estrogen therapy with high-density lipoprotein subclasses*, Arteriosclerosis and Thrombosis, vol. 13 (No. 11), p. 1654-1661, Nov. 1993.

Superko, H.R. et al., *Effect of Fluvastatin on Low-density lipoprotein peak particle diameter*, Amer. J. of Cardiology, vol. 80, p. 78-81, Jul. 1, 1997.

Dreon, D.M. et al., *Diet-gene interactions in human lipoprotein metabolism*, J. Amer. College of Nutrition, vol. 16 (No. 4), p. 313-324, 1997.

Gray, R.S. et al., *Relation of LDL size to the insulin resistance syndrome and coronary heart disease in American Indians*, Arteriosclerosis, Thrombosis & Vascular Biology, vol. 17 (No. 11), p. 2713-2720, Nov. 1997.

Barbagallo, C.M. et al., *Influence of ApoE content on receptor binding of large buoyant LDL in subjects with different DLD subclass phenotypes*, J. Amer. Heart Association, p. 466-472, 1998.

Dreon, D.M. et al., *Change in dietary saturated fat intake is correlated with change in mass of large low-density-lipoprotein particules in men*, Am. J. Clin. Nutr., vol. 67, p. 828-836, 1998.

Dreon, D.M. et al., *A very low-fat diet is not associated with improved lipoprotein profiles in men with a predominance of large, low-density lipoproteins*, Am. J. Clin. Nutr., vol. 69, p. 411-418, 1999.

Williams, P.T. et al., *Low-fat diets, lipoprotein subclasses, and heat disease risk*, Am. J. Clin. Nutr., vol. 70, p. 949-950, 1999.

Legro, R.S. et al., *Alterations in low-density lipoprotein and high-density lipoprotein subclasses among Hispanic women with polycystic ovary syndrome: influence of insulin and genetic factors*, Fertility and Sterility, vol. 72 (No. 6), p. 990-995, Dec. 1999.

Superko, H.R. et al., *Garlic powder, effect on plasma lipids, postprandial lipemia, low-density lipoprotein particle size, high-density lipoprotein subclass distribution and lipoprotein(a)*, J. Am. College of Cardiology, vol. 35 (No. 2), p. 321-326, 2000.

Dreon, D.M. et al., *Reduced LDL particle size in children consuming a very-low-fat diet is related to parental LDL-subclass patterns*, Am. J. Clin. Nutr., vol. 71, p. 1611-1616, 2000.

Havel, R.J. et al., *Genetic underpinnings of LDL size and density: a role for hepatic lipase?*, Am. J. Clin. Nutr., vol. 71, p. 1390-1391, 2000.

Krauss, R.M. et al., *Atherogenic lipoprotein phenotype and diet-gene interactions*, American Society for Nutritional Science Symposium: Nutritional and Metabolic Diversity: Understanding the Basis of Biologic Variance in the Obesity/Diabetes/Cardiovascular Disease Connection, p. 340S-343S, 2001.

Tribble, D.L. et al., *Enhanced oxidative susceptibility and reduced antioxidant content of metabolic precursors of small, dense low-density lipoproteins*, Amer. J. of Medicine, vol. 110, p. 103-110, 2001.

Krauss, R.M., *Dietary and genetic effects on low-density lipoprotein heterogeneity*, Annu. Rev. Nutr. vol. 21, p. 283-295, 2001.

Krauss, R.M., *Is the size of low-density lipoprotein particles related to the risk of coronary heart disease?*, JAMA, vol. 287, (No. 6), Letters, p. 712-713, Feb. 13, 2002.

Berneis, K. et al., *Analysis and quantitation of biotinylated apoB-containing lipoproteins with streptavidin-Cy3*, J. Lipid Res., vol. 43, p. 1155-1159, 2002.

Berneis, K. et al., *Metabolic origins and clinical significance of LDL heterogeneity*, J. Lipid Res., vol. 43, p. 1363-1379, 2002.

Takahata, Keiji. "Measurement and Generation of Nanometer-Sized Particles and its Application to the Establishment of Particle Size Standards" Measurement Research Report, Jan. 2001, vol. 50, No. 1, p. 127-p. 139 (English Translation of item "4.3 Protein" on p. 136 provided).

Japanese Office Action (including English translation) from JP Application No. 2003-544486 dated Dec. 24, 2008.

Japanese Office Action (including English translation) from Japanese Patent Application No. 2003-544486 dated Nov. 17, 2009.

FIG. 3

TABLE OF DENSITY AND PARTICLE SIZE OF THE MAJOR LIPOPROTEIN SUBFRACTIONS

|  | Density Range (gm/ml) | PARTICLE DIAMETER (Å) |
|---|---|---|
| VLDL | | |
| 1 | <1.006 | 330-700 |
| 2 | 1.006-1.010 | 300-330 |
| IDL | | |
| 1 | 1.008-1.022 | 285-300 |
| 2 | 1.013-1.019 | 272-285 |
| LDL | | |
| 1 | 1.019-1.023 | 272-285 |
| 2A | 1.023-1.028 | 265-272 |
| 2B | 1.028-1.034 | 256-265 |
| 3A | 1.034-1.041 | 247-256 |
| 3B | 1.041-1.044 | 242-247 |
| 4A | 1.044-1.051 | 233-242 |
| 4B | 1.051-1.063 | 220-233 |
| HDL | | |
| 2b | 1.063-1.100 | 98-130 |
| 2a | 1.100-1.125 | 88-98 |
| 3a | 1.125-1.147 | 82-88 |
| 3b | 1.147-1.154 | 77-82 |
| 3c | 1.154-1.203 | 72-77 |

METHOD OF ASSESSING A LIPID-RELATED HEALTH RISK BASED ON ION MOBILITY ANALYSIS OF LIPOPROTEINS

CROSS REFERENCE TO RELATED APPLICATIONS

This application is a divisional of U.S. patent application Ser. No. 11/771,862, now U.S. Patent No., 7,713,744, filed Jun. 29, 2007, entitled "Determining the Risk of Cardiovascular Disease Using Ion Mobility of Lipoproteins," which is a divisional of U.S. patent application Ser. No. 10/293,610, now U.S. Pat. No. 7,259,018, filed Nov. 12, 2002, entitled "Ion Mobility Analysis of Biological Particles," which claims priority to U.S. provisional patent application No. 60/338,214, filed Nov. 13, 2001, entitled "Ion Mobility Analysis of Biological Particles," each of these references are hereby incorporated by reference.

STATEMENT REGARDING FEDERAL FUNDING

This invention was made with U.S. Government support under Contract Number DE-AC03-765F00098 between the U.S. Department of Energy and The Regents of the University of California for the management and operation of the Lawrence Berkeley National Laboratory. The U.S. Government has certain rights in this invention.

BACKGROUND OF THE INVENTION

1. Field of the Invention

The present invention generally relates to particle size analysis and, further, to analysis of biological particles for diagnostic purposes utilizing traditional particulate size or mobility measurement devices. One aspect of the present invention more particularly relates to medical diagnostics for the quantitative and qualitative analysis of lipoprotein classes and subclasses and their relationship to the assignment of coronary heart disease and other lipid-related health risks.

2. Description of the Relevant Art

Introduction

In clinical practice, lipoprotein particle measurements are used to assess cardiovascular and other lipid-related health risks, determine treatment protocols and track the efficacy of treatment regimens. Lipoprotein particles comprise macromolecules that package cholesterol and other biochemicals, enabling them to be transported through the blood stream. The size distribution of lipoprotein particles varies among individuals due to both genetic and nongenetic influences. The diameters of lipoprotein particles typically range from about 7 nm to about 120 nm. In this diameter size range, there exist subfractions of the particles that are important predictors of cardiovascular disease. For instance, very low density lipoproteins transport triglycerides in the blood stream; high very low density lipoprotein levels in the blood stream are indicative of hypertriglyceremia. These subfractions are identified by analytical techniques that display the quantity of material as a function of lipoprotein particle size or density.

Standard Plasma Lipid and Lipoprotein Cholesterol Measurement Techniques

Typical standard lipid measurements include fasting total cholesterol, triglyceride, as well as HDL and LDL cholesterol. Currently, the most widely used method for measuring LDL cholesterol is the indirect Friedewald method (Friedewald, et al., Clin. Chem. Vol. 18, pp. 499-502, 1972). The Friedewald assay method requires three steps: 1) determination of plasma triglyceride (TG) and total cholesterol (TC), 2) precipitation of VLDL and LDL, and 3) quantitation of HDL cholesterol (HDLC). Using an estimate for VLDLC as one-fifth of plasma triglycerides $$\left(\frac{TG}{5}\right),$$

the LDL cholesterol concentration (LDLC) is calculated by the formula: LDLC=TC−(HDLC+VLDLC). While generally useful, the Friedewald method is limited in its accuracy in specific cases. Errors can occur in any of the three steps, in part because this method requires that different procedures be used in each step. The Friedewald method is to a degree indirect, as it presumes that VLDLC concentration is one-fifth that of plasma triglycerides. When the VLDL of some patients deviates from this ratio, further inaccuracies occur. Ultracentrifugation must be employed for separation and subsequent determination of LDL cholesterol for some samples, since the Friedewald method cannot be used for patients with TG over 400 mg/dL.

Procedures for Lipoprotein Subspecies Analysis

Presently, the predominant methods for lipoprotein subspecies *analysis* include nuclear magnetic resonance, the vertical auto profile, and Electrophoretic gel separation. Each of these methods will be briefly discussed below.

Nuclear Magnetic Resonance

Otvos teaches a nuclear magnetic resonance (NMR) procedure for determining the concentrations of lipoprotein subclasses, which has greater accuracy than Friedewald (U.S. Pat. No. 5,343,389, issued Aug. 30, 1994). Otvos initially obtains the NMR chemical shift spectrum of a blood plasma or serum sample. The observed spectrum of the entire plasma sample is then matched with the known weighted sums of NMR spectra of lipoprotein subclasses, which are stored in a computer software program. The weight factors that give the best fit between the sample spectrum and the calculated spectrum are then used to estimate the concentrations of constituent lipoprotein subclasses in the blood sample. This procedure has the additional advantage of being rapid.

Vertical Auto Profile

Another lipoprotein subfraction determination method that is used clinically is the Vertical Auto Profile (VAP), (Kulkarni, et al., *J. Lip. Res.*, Vol. 35, pp. 159-168, 1994). In the Vertical Auto Profile method, a flow analyzer is used for the enzymatic analysis of cholesterol in lipoprotein classes separated by a short spin single vertical ultracentrifugation, with subsequent spectrophotometry and software analysis of the resulting data. While a useful advance, this technique does not resolve the LDL into all seven subspecies *identified* by electrophoretic gradient gel separation.

Electrophoretic Gradient Gel Separation

The gel separation method is demonstrated in U.S. Pat. No. 5,925,229, issued Jul. 20, 1999, by R. M. Krauss, et al., entitled "Low Density Lipoprotein Fraction Assay for Cardiac Disease Risk," (the '229 patent), which is hereby incorporated by reference. In the '229 patent, a gradient gel electrophoresis procedure for the separation of LDL subclasses is disclosed. The LDL fractions are separated by gradient gel electrophoresis, producing results that are comparable to those obtained by ultracentrifuge. This method generates a fine resolution of LDL subclasses, and is used principally by research laboratories. However, gradient gel electrophoresis can take many hours to complete. It would be useful if gradient gel electrophoresis separation times could be shortened and the analysis simplified so that high resolution lipid analysis could be used in clinical laboratories as part of a routine screening of blood samples, and to assign a risk factor for coronary artery disease.

The gel separation method, which depends on uniform staining of all components that are subsequently optically measured, suffers from nonuniform chromogenicity. That is, not all lipoprotein particles stain equally well. The differential stain uptake produces erroneous quantitative results, in that a less staining peak may be read at a lower value than is actually present. Additionally, the nonuniform chromogenicity can result in erroneous qualitative results, in that measured peaks may be skewed to a sufficient degree as to confuse one class or subclass of lipoprotein with another.

A high-resolution assay for measuring all subclasses of LDL as well as VLDL, IDL, HDL, and chylomicron particles that would be accurate, direct, and complete, would be an important innovation in lipid measurement technology. If inexpensive and convenient, such an assay could be employed not only in research laboratories, but also in a clinical laboratory setting. Ideally, clinicians could use this information to improve current estimation of coronary disease risk and make appropriate medical risk management decisions based on the assay.

SUMMARY OF THE INVENTION

This invention provides: 1) a method for preparing plasma samples for differential mobility analysis ("DMA"), 2) a technique for measuring the size or density distribution of biological particles (preferably lipoprotein particles) based on the measured particle mobility counting rate for the number of biological particles counted per second at a specific selected mobility as a function of size, $$\left.\frac{dn^+}{dt}\right|_s,$$

or density, $$\left.\frac{dn^+}{dt}\right|_\rho,$$

of ionized biological particles sprayed into a fluid (such as air), 3) a DMA device for measuring the number of biological particles in each size class and subclass, 4) an algorithm for predicting the risk of coronary heart disease (CHD) using the biological particle (preferably lipoprotein) size or density distribution information compared to reference data for low risk, intermediate risk, and high risk patients, and 5) a particular method for determining whether a sample corresponds to a Type A, AB, or B pattern, which respectively has an associated low risk, an intermediate risk, and a high risk for CHD. Blood plasma samples are processed to separate all classes and subclasses of lipoprotein particles from bulk blood serum using steps designed ultimately for transferring the particles into the gas phase for subsequent mobility analysis. The technique preserves lipoprotein particle composition and size, and introduces no contamination into the lipoprotein particles. The electrospray process initially produces electrospray droplets with many different charge states. These multiply-charged droplets are passed in close proximity to an alpha radiation source, which produces alpha particles, or free secondary electrons, that reduces the charge state of the electrospray droplets to either neutral or single positive charges. The charged droplets may alternatively be treated in other ways to achieve a uniform charge state of no more than a single positive charge.

Subsequent volatilization of the droplet diluent results in individual lipoprotein particles having either a neutral or a single positive charge. By scanning a high voltage selection voltage that modifies a mobility selection, lipoprotein particle gas-phase mobility can be measured over a range of mobilities. When the scanned mobilities are counted over a scan range, a mobility distribution can be developed. Personnel skilled in reading the lipoprotein mobility distribution can make direct conclusions regarding the cardiac risk for the patient.

An inverse linear relationship between lipoprotein mobility and size allows the mobility distribution data to be converted to a particle size distribution, thereby providing a way to display a spectrum, or distribution, of the number of particles counted per unit time vs. particle size. Given a constant time basis, this measurement can be regarded as number of particles vs. particle size, and can be related back to a quantitative fractional distribution of lipoproteins in the original sample. The resulting lipoprotein particle size distribution is comprised of component regions. These regions, in turn, distinguish the quantity and types of lipoprotein particles in the original serum sample. By determining the relative location of certain peaks in certain of the regions, a prediction can be made as to the cardiac risk. The size distribution may additionally be converted into a distribution of the number of particles vs. density for more traditional comparison of lipoprotein densities.

The present invention provides a method for determining a cardiovascular disease in a patient comprising providing a biological sample from a patient; obtaining a mobility distribution of charged lipoprotein particles from the sample by electrospraying the lipoprotein particles so that the particles are provided in a charged state; delivering the lipoprotein particles to a differential mobility analyzer; comparing the mobility distribution of lipoprotein particles from the patient to a reference lipoprotein particle mobility distribution; and determining whether the patient has a cardiovascular disease based on the comparison. In one embodiment, the charged lipoprotein particles are at least one of VLDL, IDL, LDL, HDL or their subclasses. In another embodiment, the biological sample is blood, plasma or serum. In another embodiment, the charged lipoprotein particles are classified on the basis of the mobility distribution. The method may further comprise converting the mobility distribution of charge reduced lipoproteins to at least one of the following measurements prior to determining the cardiovascular disease of the patient: a particle mobility, a particle size, a particle density, a particle mass, a number of particles in a size interval and an amount of particle mass in a size interval. In one embodiment, the cardiovascular disease is coronary heart disease. In another embodiment, step (d) is carried out by a deterministic algorithm.

The present invention also provides a method for determining a cardiovascular condition in a patient, comprising providing a biological sample from a patient; obtaining a mobility distribution of charged lipoprotein particles from the sample by electrospraying the lipoprotein particles so that the particles are provided in a charged state; delivering the lipoprotein particles to a differential mobility analyzer; comparing the mobility distribution of lipoprotein particles from the patient to a reference lipoprotein particle mobility distribution; and determining whether the patient has a cardiovascular condition based on the comparison. In one embodiment, the charged lipoprotein particles are at least one of VLDL, IDL, LDL, HDL or their subclasses. In another embodiment, the biological sample is blood, plasma or serum. In another embodiment, the charged lipoprotein particles are classified on the basis of the mobility distribution. The method may further comprise converting the mobility distribution of charge reduced lipoproteins to at least one of the following measurements prior to determining the cardiovascular condition of the patient: a particle mobility, a particle size, a particle density, a particle mass, a number of particles in a size interval and an amount of particle mass in a size interval. In another embodiment, the cardiovascular condition is cardiac disease or a predisposition to develop cardiovascular disease.

The present invention also provides a method for determining a predisposition to developing a cardiovascular disease or condition in a patient comprising providing a biological sample from a patient; obtaining a mobility distribution of charged lipoprotein particles from the sample by electrospraying the lipoprotein particles so that the particles are provided in a charged state; delivering the lipoprotein particles to a differential mobility analyzer; comparing the mobility distribution of lipoprotein particles from the patient to a reference lipoprotein particle mobility distribution; and determining whether the patient has a predisposition to develop a cardiovascular disease or condition based on the comparison. In one embodiment, the charged lipoprotein particles are at least one of VLDL, IDL, LDL, HDL or their subclasses. In another embodiment, the sample is blood, plasma or serum. In another embodiment, the charged lipoprotein particles are classified on the basis of the mobility distribution. The method may further comprise converting the mobility distribution of charge reduced lipoproteins to at least one of the following measurements prior to determining the predisposition to develop the cardiovascular disease or condition of the patient: a particle mobility, a particle size, a particle density, a particle mass, a number of particles in a size interval and an amount of particle mass in a size interval. In another embodiment, step (d) is carried out by a deterministic algorithm.

BRIEF DESCRIPTION OF THE DRAWINGS

FIG. 3 is a close up cross-sectional view of a properly operating axisymmetric electrospray capillary with a stable Taylor cone.

DETAILED DESCRIPTION OF THE PREFERRED EMBODIMENT

Definitions

"Biological particle" means a material having a non-covalently bound assembly of molecules derived from a living source. Examples are lipoprotein particles assembled from apolipoproteins and lipids; viral components assembled from non-covalently bound coat proteins and glycoproteins; immune complexes assembled from antibodies and their cognate antigens, etc., but not entire cells.

"Physiological sample" means a sample obtained from an organism, such as blood, tissue, pulp, cytoplasm, etc.

"CHD" means coronary heart disease.

Figure 2:
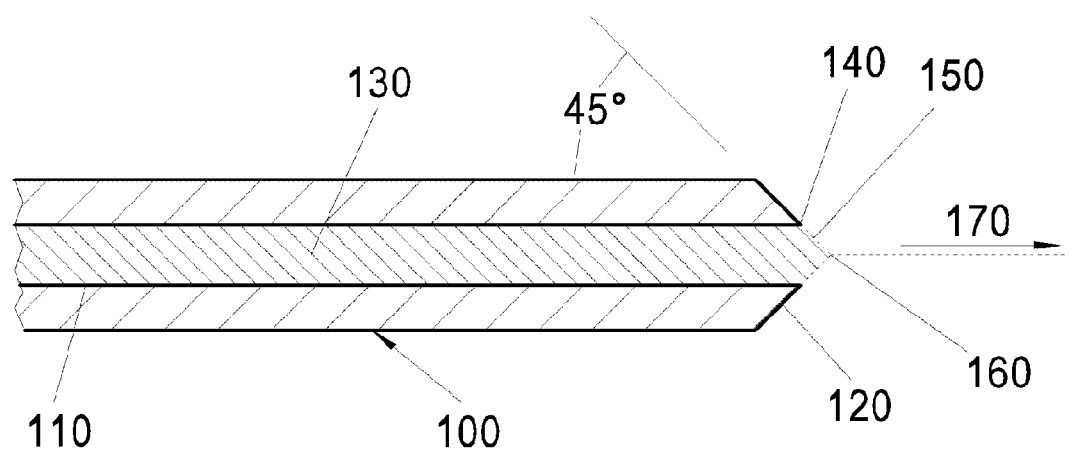
FIG. 2 is a table of major lipoprotein classes, subclasses, densities and particle sizes as reported from gel electrophoresis results.

"VLDL, IDL, LDL, and HDL" are described by class name, acronym, subclass, and density range as shown in FIG. 2.

"Chylomicrons" means biological particles of size 70-120 nm, with corresponding densities of less than 1.006 g/mL.

"Differential Mobility Analyzer" means a device for classifying charged particles on the basis of their ion electrical mobility. When the particles have a known uniform charge, the size of the particles classified may be determined from their mobility.

"Lp(a)" means biological particles consisting of LDL covalently attached to the protein lipoprotein A.

"Lipoprotein particles" means particles obtained from mammalian blood, comprising apolipoproteins biologically assembled with noncovalent bonds to package cholesterol and lipids. Lipoprotein particles preferably refer to biological particles having a size range of 7 to 1200 nm. Lipoprotein particles, as used herein, essentially include VLDL, IDL, LDL, HDL and chylomicrons.

"Centrifugation" means separation or analysis of substances in a solution as a function of density and density-related molecular weight by subjecting the solution to a centrifugal force generated by high-speed rotation in an appropriate instrument.

Figure 5:
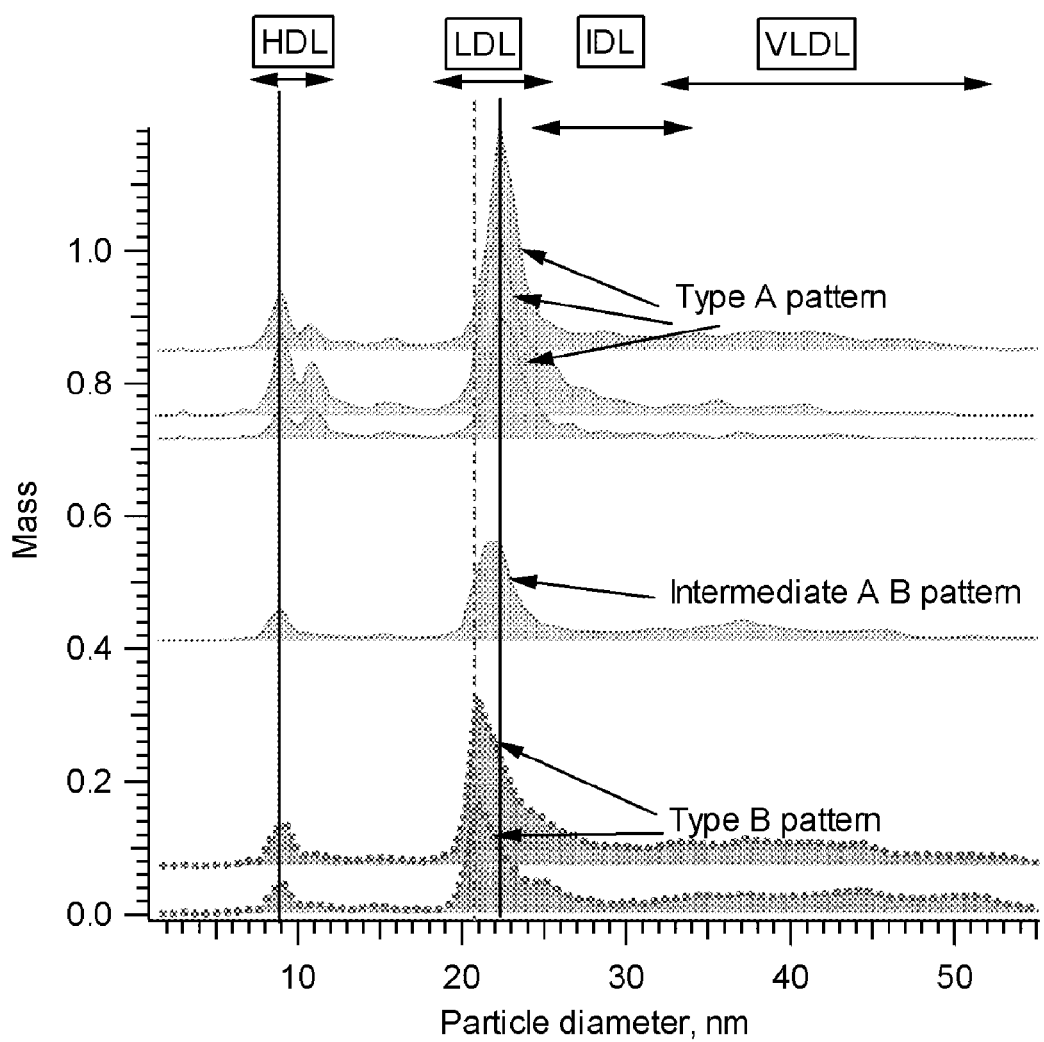
FIG. 5 is a scanning differential mobility analyzer output of mass-offset lipoprotein size distributions obtained from six individuals.

"Pattern A" is the designation applied to individuals having a characteristic lipoprotein particle distribution indicating a relatively low risk for CHD, as illustrated in FIG. 5.

"Pattern B" is the designation applied to individuals having a characteristic lipoprotein particle distribution indicating a relatively high risk for CHD, as illustrated in FIG. 5.

"Pattern AB" is the designation applied to individuals having a characteristic lipoprotein particle distribution indicating an intermediate risk for CHD, as illustrated in FIG. 5. Pattern AB has a distribution with some of the characteristics of both Pattern A and Pattern B.

"Predisposition" as used herein is substantially synonymous with risk, inclination, tendency, predilection, or susceptibility.

"Reference Size Distribution" means a lipoprotein particle size distribution such as Patterns A, B, or AB as further discussed in connection with FIG. 5.

"Computer readable medium" means any source of organized information that may be processed by a computer, including but not limited to: a magnetically readable storage system; optically readable storage media such as punch cards or printed matter readable by direct methods, optical reflectance and transmission scanning, or methods of optical character recognition; other optical storage media such as a compact disc (CD), digital versatile disc (DVD), rewritable CD and/or DVD; electrically readable media such as programmable read only memories (PROMs), electrically erasable programmable read only memories (EEPROMs), field programmable gate arrays (FPGAs), flash random access memory (flash RAM); and remotely transmitted information transmitted by electromagnetic or optical methods.

"Distribution" means a generalized function of one or more variables, and commonly depicted as a scatter chart, graph, plot, or histogram.

Overview of Ion Mobility Analysis of Biological Particles

Figure 1:
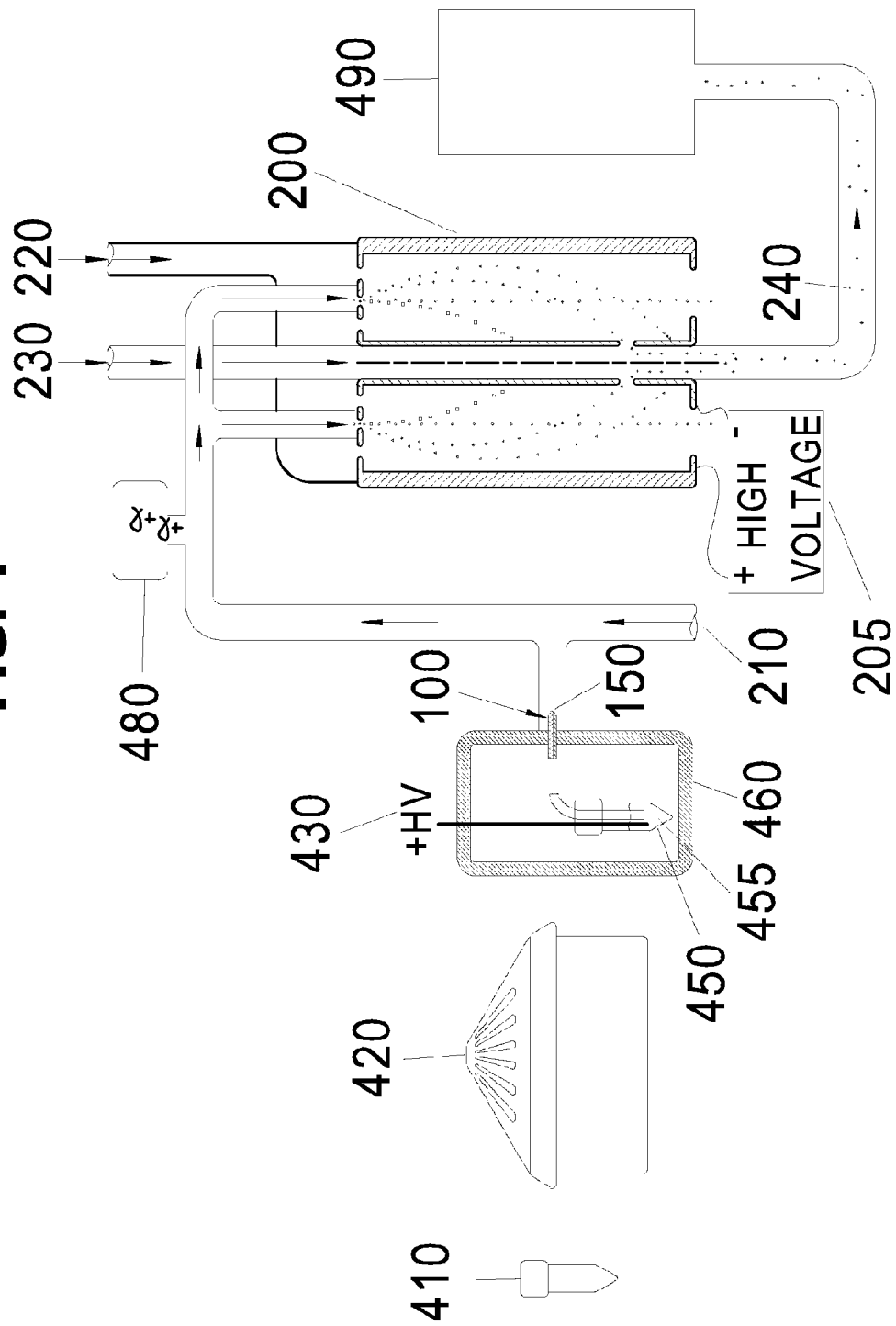
FIG. 1 is an overview of the ion mobility analysis of biological particles hardware and analytical sequence.

FIG. 1 depicts the major functional components involved in biological particle ion mobility analysis. A sample is placed in a microcentrifuge tube 410, which is then placed in an centrifuge 420 to remove undesirable components, such as Lp(a), and other cellular components as described below in Section D "Preparation of Purified Lipoprotein Particle Samples." After removal of cellular components and Lp(a), as well as further density ultracentrifugation to select only lipoprotein materials, a sample solution 455 is placed in a testing microcentrifuge tube 450, which is in turn placed in a pressurized chamber 460. A high voltage variable power supply 430, positively biases the pressurized chamber 460, and the sample solution 455, through a Pt wire 435. The positive bias and higher relative pressure causes a capillary 100 to form a Taylor cone 150 emitting particle droplets from the pressurized chamber 460. FIG. 3 more fully details the capillary 100.

Still referring to FIG. 1, once the droplets are formed, a dry gas 210 propels the droplets into an emission region of an alpha radiation source 480, which reduces the charge state of the droplets to no more than one positive charge per droplet as the droplets containing components other than the volatile diluent dry to single particles. The charged droplets may alternatively be treated with other methods to achieve a uniform charge state of no more than a single positive charge. One such other method is to use an alternating current corona, which produces secondary electrons having the same charge state reduction as an alpha source.

Figure 4:
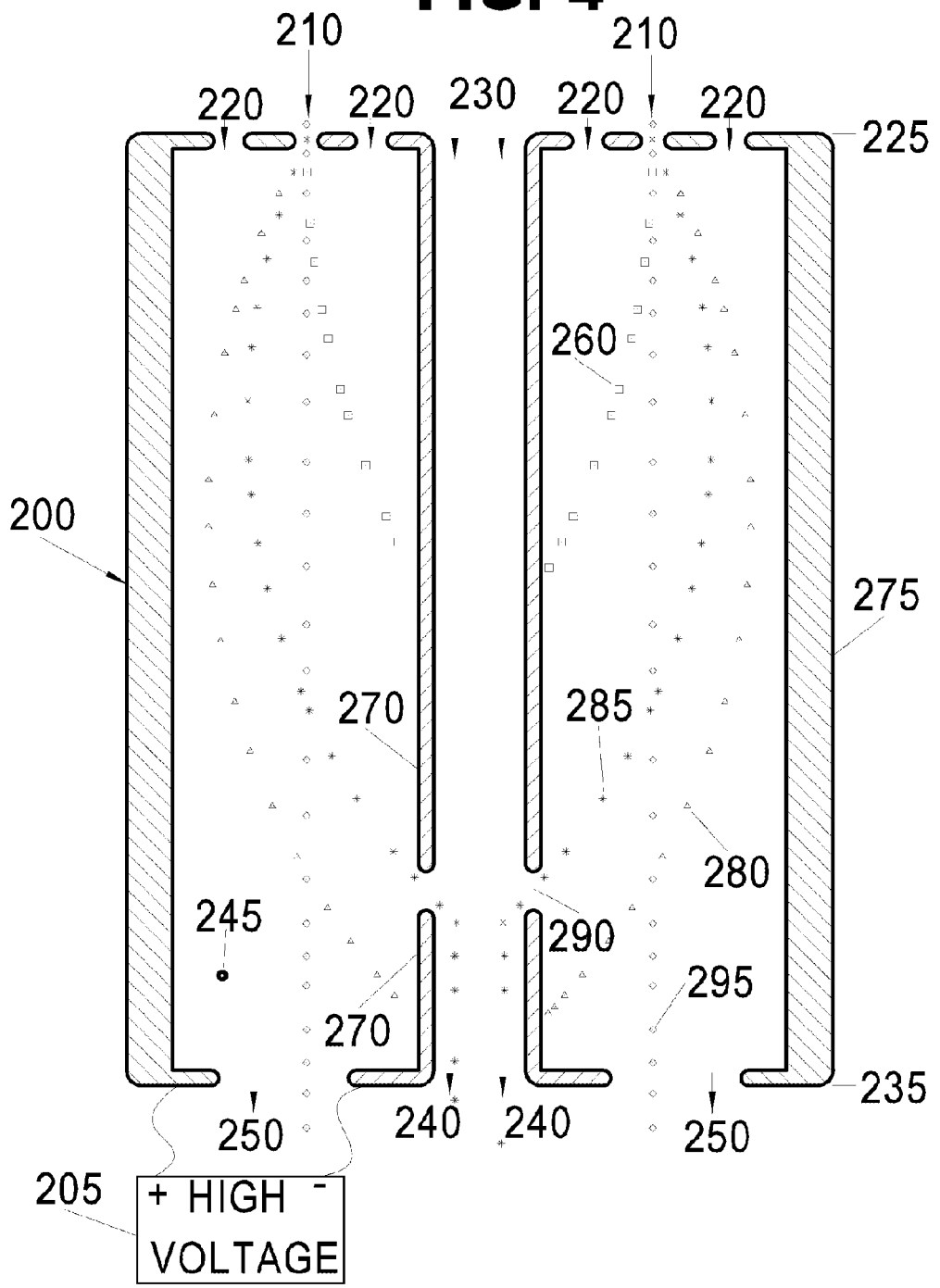
FIG. 4 is a cross sectional view through the centerline of an axisymmetric differential mobility analyzer.

After charge reduction, the dry gas 210 propels the particles into a differential mobility analyzer 200, which is shown in more detail in FIG. 4. A laminar flow excess gas 220, as well as an additional dry gas 230 flow is introduced to match the velocity of the dry gas 210 flow. By varying a high voltage power supply 205, the particles carried by the combined flows are selected into a mobility selected particle 240 flow, which in turn flows into a particle counter 490.

Particle counter 490 is preferably in communication with a computer system (not shown) having storage capability onto one or more computer readable media for recording a scanned distribution output of the differently sized particles. As discussed below under Section F "Differential Mobility Analysis," the single positively charged particles, the fixed dry gas 210 and additional dry gas 230 flows, and particular voltage setting of the scanned high voltage power supply 205, classifies a selected particle stream 285 to enter into an exiting annular selection slit 290, the selected particle stream 285 having particles with a particular mobility and corresponding particle size.

One feature of this invention is that loose, non-covalently bonded biological particles can be processed through this system without losing their biological identity or breaking apart. In particular, lipoprotein particles (e.g. VLDL, IDL, LDL, and HDL and their subclasses) can be processed in such a fashion so that their particle mobilities, and hence size and density, can be quickly determined, without lipoprotein particle breakdown.

Once a relationship is known between particle size and density, size or mobility distributions may be converted into distributions of: a particle mass, a density $\mu g/cm^3$ of original plasma, a number of particles in a size interval, and an amount of particle mass in a size interval.

Lipoprotein Particles

Lipoproteins are complex macromolecules found in human blood plasma that package lipids into lipoprotein particles. Among other functions, lipoprotein particles in the circulatory system transport cholesterol for cellular use. Lipoprotein particles are subdivided into a variety of classes and subclasses based on density as well as particle size. Lipoprotein particle density can be determined directly by equilibrium density ultracentrifugation and analytic ultracentrifugation. Lipoprotein particle density may also be determined indirectly based on particle size and a known relationship between particle size and density. Particle size may be determined by several methods including gel electrophoresis.

FIG. 2 is a table of the present standard classes and subclasses that have been assigned to various lipoprotein fractions using traditional gel electrophoresis measurements: very low density lipoproteins (VLDLs) with subclasses VLDL I and II, intermediate density lipoproteins (IDLs) with subclasses IDL I and II, low density lipoproteins (LDLs) and high density lipoproteins (HDLs), which typically includes several subclasses, such as HDL IIa, IIb, IIIc, IIIb, and IIIc.

Chylomicrons are not included in FIG. 2, as chylomicrons have not been found to have any clinical significance in the prediction of heart disease.

Ultracentrifugally isolated lipoprotein particles can be analyzed for flotation properties by analytic ultracentrifugation in two different salt density backgrounds, allowing for the determination of hydrated LDL particle density, as shown in Lindgren, et. al, *Blood L is ids and Lipoproteins: Quantitation, Composition and Metabolism*, Ed. G. L. Nelson, Wiley, 1992, p. 181-274, which is incorporated herein by reference.

The LDL class, as indicated in FIG. 2, can be further divided into seven subclasses based on density or particle diameter by using a preparative separation technique known as equilibrium density gradient ultracentrifugation (EDGU). It is known that elevated levels of specific LDL subclasses, LDL-IIIa, IIIb, IVa and IVb, is a clinical finding which correlates closely with increased risk for CHD, including atherosclerosis.

Determination of the total serum cholesterol level and the levels of cholesterol in the LDL and HDL fractions are routinely used as diagnostic tests for coronary heart disease risk. Lipoprotein class and subclass distribution is a more predictive test, however, since it is expensive and time-consuming, it is typically ordered by physicians only for a limited number of patients.

It should be noted that the values used in FIG. 2 for sizes are determined by gel electrophoresis methods. With the ion mobility methods disclosed here, it has been observed that all measurements of lipoprotein particle diameter obtained with ion mobility are shifted to smaller diameters compared to the data obtained with gel electrophoresis. It is surmised that this difference is caused by calibration of the gels. The shift appears to be linearly related with approximately:

0.86*gel diameter=ion mobility diameter

The observed differences between ion mobility diameters and gel electrophoresis diameters may also be due to the fact that the lipoprotein particles are distorted as they bump into the gel matrix under the influence of the electrophoresis gel's intrinsic impressed electric field. The size difference may also be due to historical data used to convert particle density (obtained from analytic ultracentrifuge separations) to particle size obtained from electron microscopy. FIG. 2 presents the lipoprotein sizes accepted for gel electrophoresis runs as published in common scientific literature. It is the inventors' opinion that ion mobility sizes may be more accurate than gel sizes, however, this needs to be confirmed.

Preparation of Purified Lipoprotein Particle Samples

Generally, sample preparation comprises the following steps: taking a blood sample, separation of the blood plasma from the cellular matter, removal of non-lipoprotein proteins from the plasma by one of several methods, such as ultracentrifugation or adsorption on affinity gels, dialysis filtration to remove density adjusting components that would affect particle volatility and/or size, addition of volatile reagents to facilitate electrospray droplet formation, dilution of lipoprotein particle sample solution, and adjustment of sample solution pH.

A 50 to 100 µL fasting blood sample is initially taken. Chylomicrons are not typically present in people who have been fasting for a period of at least 12 hours, so overlap of VLDL particle sizes and chylomicron sizes is eliminated by fasting. The sample is then initially spun in a centrifuge. The sample is preferably spun for approximately 10 minutes at 2000 gravities, sufficient to remove the cellular components from the sample. During this process, the more dense cellular components stratify at the bottom of the sample. A remaining less dense plasma specimen on top is then drawn off.

The plasma specimen is then density-adjusted to a specific density using high purity solutions of sodium chloride (NaCl) and sodium bromide (NaBr). In one embodiment, the specific density is chosen to be greater than or equal to the highest density of the lipoprotein material to be analyzed, so that the lipoprotein material floats when density stratified. These densities may be found in the FIG. 2 table of lipoprotein classes, subclasses, densities, and sizes. By sequentially centrifuging from lowest density to highest density of the density adjustment, the various classes and subclasses of lipoproteins may be sequentially extracted.

In the preferred method used in this invention, instead of a series of sequential density adjustments followed by centrifugation, just a single density adjustment using NaCl and NaBr salts is performed. A single specific density is chosen for density adjustment in the preferred embodiment. The sample density adjustment can be selected within the range of 1-1.21 g/mL according to the densities in FIG. 2 to separate a class of lipoproteins having equal or lesser density. In the preferred embodiment, a density adjustment to 1.21 g/mL is made. In this manner, all HDLs, IDLs, LDLs, and VLDLs are simultaneously extracted, since they have densities less than 1.21 g/mL.

The density-adjusted plasma sample is then ultracentrifuged in a common commercially available 100 µL ultracentrifuge tube for approximately 18 hours at 100,000 gravities, or $10^6$ m/s$^2$ to separate the non-lipoprotein proteins from the lipoprotein particles. Non-lipoprotein proteins, particularly albumin, are then removed from the plasma specimen, preferably by this ultracentrifugation step. The lipoprotein particles float to the top of the sample during ultracentrifugation.

Lp(a) is another type of lipoprotein particle found in serum having a molecular composition distinct from IDL and LDL particles. Lp(a) has a particle size that overlaps with LDL and IDL particles and therefore will interfere with particle size analysis when Lp(a) particles are present in serum. Although some patients have naturally occurring low Lp(a) concentrations, it is a good practice to remove the Lp(a) prior to LDL particle size measurements to preclude otherwise inaccurate measurements for those patients who do have significant Lp(a) concentrations. In this manner, any potential Lp(a) size interference problem is avoided.

In sample solutions where Lp(a) has not been removed, up to half of the LDL measurement can be comprised of Lp(a). Therefore, before electrospray analysis Lp(a) is preferably removed from the plasma sample. This removal can be achieved by solid phase absorption of the Lp(a) protein using either lectin or specific antibodies attached to a matrix. Lp(a) concentration can then be measured separately (e.g. by immunoassay) or by the difference between the immunoassay results using absorbed and unabsorbed plasma. Lp(a) is most preferably removed by lectin affinity chromatography. The Lp(a) removal step preferably follows density adjustment and ultracentrifugation. It precedes dialysis of the selected 1.21 g/mL fraction.

The lowest density, top portion, of the ultracentrifuged sample is then drawn off for subsequent dialysis as a liquid sample containing lipoprotein particles. This liquid is then placed behind a 10,000 Dalton molecular weight cutoff filter, to retain the lipoprotein particles behind the filter, yet freely allow diffusion of $H_2O$, NaCl and NaBr ionic components. The filter, with the liquid containing the density adjusting NaCl and NaBr, is immersed in 0.22 μm particle-filtered, 18 Meg-ohm deionized water to allow the NaCl and NaBr to reach concentration equilibrium with the surrounding water. In this fashion, the NaCl and NaBr, which otherwise would have affected particle weight during mobility measurement, are removed, or dialyzed. In the laboratory, it has been found sufficient to place the cutoff membrane in contact with water, and simply deposit a drop of sample to the top of the membrane. The NaCl and NaBr levels in the drop of sample then reach equilibrium with the water diluent.

The sample solution is then prepared in a volatile aqueous buffer at sufficiently near neutral pH (pH 7.0), so as to prevent the lipoprotein particles from disintegrating into one or more of their constituent molecules. The preferred buffer solution is 20-30 mM, preferably 25 mM, ammonium acetate in particle-filtered 18 Meg-ohm deionized water with pH adjusted to neutral with high purity ammonium hydroxide. It is critical to prepare the ammonium acetate and ammonium hydroxide solutions with very high purity reagents in order to prevent contamination of the lipoprotein particles, which would subsequently affect the particle mobility measurements.

The volatile aqueous buffer serves three principal functions: 1) to dilute the sample sufficiently so that, when electrosprayed, only one lipoprotein particle is contained within each electrospray droplet, 2) to provide for electrical conductivity so that the capillary bore sample contents are uniformly at approximate equipotential with the high voltage power source, and 3) to impart a higher vapor pressure to the bulk solution, thereby improving volatility of the diluted sample and hastening droplet drying time. Although ammonium acetate has been used here, people skilled in the art could arrive at several alternative formulations achieving the same three functions.

The amount of insoluble material and the residue remaining after dilution and subsequent volatilization are important specifications for choosing a particular quality of reagent. These quantities should be minimized; preferably each reagent should have less than 0.005 weight percent of impurities. Subsequently, the lipoprotein sample is either prepared in solution with the reagent or diluted with this reagent to about $10^{11}$ particles per mL or less.

At lipoprotein particle concentrations of less than $10^{11}$ particles per mL, no more than one lipoprotein particle should be present in a single electrospray droplet. By designing the dilution process to have only one lipoprotein particle in an electrospray droplet, a potential aliasing problem of artificially combining lipoprotein particle clusters, and thereby detecting the lumped cluster as a larger lipoprotein, is avoided. Restating this issue, if two small weight lipoprotein particles arrive in a single droplet, then the resulting size measurement of the compound particle is much larger, and is not representative of the original lipoprotein sample. Thus, if aliasing were to occur, two or more small HDL particles could be measured as a single VLDL particle, distorting the mobility measurement, and further indicating an incorrect corresponding particle size distribution.

The lipoprotein particles suspended in the ammonium acetate solution are then electrosprayed. The electrospray is fed by pumping the sample solution at a rate of about 50 mL per minute through a small capillary tube, preferably an Osage number 062442 capillary. Between 20 and 50 μL of sample solution is placed in a microcentrifuge tube and the entrance to a silica capillary having a 20 μm interior diameter is placed into this sample solution. The microcentrifuge sample tube and the entrance end to the capillary are sealed in a positive pressure container. A positive differential pressure, on the order of 3 psig, is applied across the capillary, producing a flow of sample solution through the capillary. The outlet side of the capillary, maintained at approximately ambient atmospheric pressure, is inserted into an electrospray droplet generator, preferably a TSI Model 3480 Electrospray Aerosol Generator (TSI, Incorporated, St. Paul, Minn.).

Electrospray of Samples

The electrospray capillary used in this invention is shown axisymmetrically in FIG. 3. The capillary body 100 has a hollow core, through which a sample solution 130 is transported. It is preferred to use a capillary 100 that has been passivated with a coating such as a methyl derivatization along the hollow core of the interior bore 110 of the capillary 100, so that substances found in the sample solution 130 are not adsorbed as the sample solution 130 is electrosprayed, as such adhesion would tend to clog the capillary, rendering it unusable until successfully cleaned. It has been found that a capillary derivatized with a methylating reagent replaces silanol and Si—O— groups on the interior bore 110 with methyl groups, which thereby minimizes adsorption of sample onto the capillary, and subsequent clogging.

Stable electrosprays are obtained when the capillary 100 is about 25 cm long and a positive voltage of about 2 kV is applied to the sample 130. This is accomplished, as shown in FIG. 1, by placing a Pt wire 435 into the testing microcentrifuge tube 450 and in electrical contact with the sample solution 435. The Pt wire 435 is connected to the positive polarity of a high voltage variable power supply 430. It is also necessary to taper the wall of the outlet end of the capillary 120 to produce a truncated flat-tipped cone 140 with about a 90° included taper. The tapered area of the capillary thus resembles a truncated cone.

Refer now to FIG. 3. The tapered outlet end 120 of the capillary 100 is produced by placing a capillary 100 securely into a pin-vise mounted on a 50 rpm DC motor, and subsequently grinding an approximately 45° angle from the longitudinal direction of the capillary.

Electrospray occurs at the flat-topped tapered outlet end of the capillary 120. The meniscus of the exiting sample 130 liquid takes on the characteristic shape of a Taylor cone 150, typical of stable electrosprays, but only a sharp-tipped cone 160 can be seen during the electrospray of highly conductive liquids typically used because the droplet stream 170 that forms is comprised of droplets too tiny to scatter light and thus be microscopically observed.

The droplet stream 170 is carried into a small chamber by a laminar flow of $CO_2$ and air, established according to TSI factory recommendations, where they are exposed to an alpha radiation source 480 (as previously shown in FIG. 1), which, as the droplet diluent evaporates, lowers the droplet net charge state to zero or one. The initial droplet size is typically approximately 150 nm in diameter.

As discussed in Section B "Overview of Ion Mobility Analysis of Biological Particles," the droplets dry rapidly in the flow of $CO_2$ and air and desolvate forming neutral or singly charged lipoprotein particles. The lipoprotein particles carry the same amount of charge as did the droplets that were initially electrosprayed. In typical implementations, drying and charge reduction may take place concurrently to prevent Coulomb forces breaking apart droplets, and here lipoprotein particles. The resulting gas-borne particles are primarily charge neutral or carry one positive charge. The alpha-source charge reduction process produces a reliable, well-characterized stream of charged particles. In this case, well characterized means that, although the fraction of singly charged particles depends on particle diameter, the relationship between diameter and the fraction of the particles carrying a single charge is well established. The electrospray aerosol generator delivers neutral and singly-charge lipoprotein particles to the input of a differential mobility analyzer 200 where the size distribution of the particles is determined.

Other methods may be used to ensure that an entering stream of charged particles exits with particles having no more than a single positive charge. One of these methods include using an alternating current corona to produce secondary electrons having the same charge state reduction as an alpha radiation source.

Differential Mobility Analysis

Ion electrical mobility analysis is a technique to determine the size of a charged particle undergoing analysis when the charged particle is exposed to an electric field. Below follows the analytical method used to determine the size of the charged particle.

Ion electrical mobility is a physical property of an ion and is related to the velocity an ion acquires when it is subjected to an electrical field. Electrical mobility, Z, is defined as $$Z = \frac{V}{E}$$

where V=terminal velocity and E=electrical field causing particle motion. Furthermore, particle diameter can be obtained from $$Z = \frac{neC_c}{3\pi\eta d}$$

where n=number of charges on the particle (in this case a single charge), e=1.6×10⁻¹⁹ coulombs/charge, $C_c$=particle size dependent slip correction factor, η=gas viscosity, and d=particle diameter. Solving for d, we obtain $$d = \frac{neC_c}{3\pi\eta}\frac{E}{V}$$

Thus we obtain an explicit relationship for particle diameter as a function of known parameters. By setting the parameters to different values, different particle diameters of the charged particles may be selected as further described below. In particular, it is easiest to vary E, the electric field strength acting upon the charged particle.

A differential mobility analyzer separates the charged input lipoprotein particles according the their diameter and charge. A preferred differential mobility analyzer is a TSI model 3080 Electrostatic Classifier.

Now referring to FIG. 4, a cross section through the centerline of a typical axisymmetric differential mobility analyzer 200 is shown. The analyzer is designed and operated to transmit only singly charged positive ions of a particular size 285 through an exiting annular selection slit 290 in the instrument. For purposes of illustration there are several particles shown that are not at the correct selection size 285: neutral particles 295, and charged smaller particles 260 and charged larger particles 280.

The differential mobility analyzer 200 is housed in a cylinder canister 275 having a hollow cylindrical area 245 with a centrally placed tube 270. The centrally placed tube 270 comprises an annular selection slit 290 through which particles (e.g. 285 from the hollow cylindrical area 245) pass when a certain electric field exists. Particles 285 enter the annular selection slit 290 as a function of the size of the particle and the electromotive force applied to the particle. An electromotive force results from the application of a selection voltage applied from high voltage source 205 to centrally placed tube 270 and cylinder canister 275. Once a particle 285 enters centrally placed tube 270 through selection slit 290, the gas flow 230 through the centrally placed tube 270 carries particle-laden gas flow 240 to a particle-counting device 490 (as shown in FIG. 1).

In FIG. 4, four different types of particles are shown for purposes of illustration. The four different symbols represent singly charged lipoprotein particles having three different sizes 260, 280, and 285, and an uncharged particle 295. When a high voltage source 205 is applied between the centrally placed tube 270 and the outer cylinder 275, the positively charged particles begin to move towards the centrally placed tube 270 at a radial velocity determined by the balance between the forces exerted by the electric field strength and the viscous resisting force due to the drag of the particle moving through the ambient medium.

Since the viscous drag is related to the size of the particle, for the same electromotive force, a smaller particle, having a smaller cross sectional area, will have a smaller drag, will be most affected by the electromotive force, and will consequently have a higher mobility. Correspondingly, a larger particle will have a larger cross sectional area, and will be least affected by the same electromotive force, and consequently have a lower mobility.

The axial gas velocity moving from the top of the analyzer 225 to the bottom of the analyzer 235 influences the location where the particles impinge the centrally placed tube 270 by vector velocity component addition. FIG. 4 shows that one of the types of particle ions 285 has a mobility that deposits it into a detection slit 290 that leads the selected ions away to a detector 490. That is, only a small distribution of particle sizes distributed about the selected particle size exits detection slit 290 at a specified high voltage 205 at a specific laminar gas velocity in the hollow cylindrical area 245.

Particle laden dry gas 210 introduces the particles into the differential mobility analyzer 200, with a laminar excess gas flow 220 introduced so as to minimize turbulent eddies of any sort. An additional dry gas 230 is introduced at the top of the analyzer 225, ultimately exiting the bottom of the analyzer 235 as mobility-classified particle flow 240.

In FIG. 4, only those particles with a particular size 285 are presently being selected. Smaller sized particles 260 impinge on the center tube before the detection slit 290. Larger sized particles 280 either impinge after the slot, or are carried away with the bulk gas flow, but in neither case are measured. Uncharged particles 295, are unaffected by the electromotive force, thus pass through the exit gas stream 250 without passing through the detection slit 290. Mobility spectra may then be obtained by scanning the high voltage source 205 applied to the centrally placed tube 270 and cylinder canister 275 through a range of voltages corresponding to the sizes of the particles of interest. As the differential voltage is scanned each of the three ions will be guided to hit the slit and pass on to a detector located downstream. In this example, the small 260, medium 285, and large particles 280 may respectively represent HDL, LDL, and VLDL.

The selectable differential mobility analyzer operates by counting the number of charged biological particle ions, $dn^+$, in a defined sampling time, dt, at a specific selected size, s, resulting in a size count rate output of $$\left.\frac{dn^+}{dt}\right|_s,$$

The selectable differential mobility analyzer can be scanned over the desired specific size range to result in an output of charged biological particle ions counted in the defined sampling time versus size. Since the relationship between particle size and density is well understood, the size count rate output above can in turn be converted to data set of the number of biological particles counted per second at a specific density, $$\left.\frac{dn^+}{dt}\right|_\rho,$$

versus density, ρ.

We now look at the particular case where the biological particles are lipoproteins. In this case, a scanning size range of 3 nm to 120 nm is appropriate, corresponding to the size of the least and most dense lipoproteins present in human patients. Once the scanned data set is produced in the traditional format of the number of lipoprotein particles counted per second at a particular size, the specific quantity of lipoprotein versus density can be calculated. By numerically integrating the amount of lipoprotein within a density range corresponding to the various lipoprotein classes and subclasses, traditional analysis of cardiac heart risk may be assessed.

Data Acquisition and Analysis

The detector 490 used to record the mobility spectrum is a condensation particle detector, preferably a Model 3025A Condensation Particle Detector from TSI. The condensation particle detector draws particles such as lipoprotein particles through a supersaturated vapor condensation chamber and allows the vapor to condense onto the particles, which act as condensation nucleation sites. The device is sensitive at the single particle level because every lipoprotein particle nucleates condensation and gives birth to a solvent droplet. A single lipoprotein particle becomes completely covered inside each condensation droplet. The condensation process, in effect, magnifies the size of lipoprotein particles and causes them to grow from 10's of nm in diameter to several μm in diameter.

The μm-scale droplets efficiently scatter light into a photodetector as they pass through a laser beam. The resultant droplets scatter light sufficiently to allow for counting individual droplets by measuring changes in transmission or reflectance (scatter) in the laser beam or other light source. Since only a single lipoprotein particle is contained in each droplet, this then becomes a method for indirectly counting single lipoprotein particles.

Lipoprotein particle density measurement in the near-atmospheric gas-phase by particle mobility measurement provides a new way to rapidly determine the size distribution of the lipoprotein particles. Referring to FIG. 2, a table is shown including the density and particle size of the major lipoprotein subfractions. Since the size and density of lipoprotein particles correlate very well, it is straightforward to calculate one in terms of the other. This correlation may be shown in a plot of measured diameters and corresponding densities, which are curve fit by a line. This is shown in FIG. 6 and discussed in Section J "Linearity Versus Density." Thus any lipoprotein particle mobility measurement of a particular size can be related to its corresponding particle density.

A mobility spectrum of six typical lipoprotein samples obtained from human blood is presented in FIG. 5. Each lipoprotein particle sample solution, prepared as previously discussed, was diluted to less than $10^{11}$ lipoprotein particles per mL with a solution of 25 milliMolar ammonium acetate. The sample was electrosprayed at a rate of 50 mL per min using a positive 1850 volts to create a well-formed, stable electrospray. A stable electrospray refers to a lack of visible fluctuations in the Taylor cone. A flow of 0.5 L per min $CO_2$ was combined with 1.0 L per min of dry air to carry the electrospray droplets through a charge neutralizer, through a differential mobility analyzer, and into a condensation particle detector. The resulting spectrum of lipoprotein particles is displayed in FIG. 5, which will be more thoroughly described below.

Recall that there is a scalar difference between the gel electrophoresis lipoprotein sizes and those obtained by differential mobility analysis. The scale factor relates 0.86*gel diameter=ion mobility diameter, shifting the mobility sizes of FIG. 5 down by 86% to correspond with the lipoprotein classes and subclasses of FIG. 2.

Example of a Typical Sample Run

Refer now to FIG. 1 depicting the hardware components involved in the practice of ion mobility analysis of biological particles, specifically lipoproteins. The sample solution comprises 25 milliMolar ammonium acetate in an aqueous solution buffered to near neutral pH.

Between 10 and 50 μL of sample solution is introduced into small plastic vial, preferably a 1.5 mL microcentrifuge tube 410. The microcentrifuge tube 410 has preferably been ultracentrifuged as previously described in an ultracentrifuge 420, however, other methods such as immunoabsorption or lectin affinity binding can be used to remove the Lp(a) that would otherwise distort the measurement of lipoproteins. The testing microcentrifuge tube 450 is in turn installed in a pressurized chamber 460 on the electrospray generator. About 3 psig of positive pressure is applied to the pressurized chamber 460, forcing the sample solution 455 to flow through the electrospray capillary 100 and out the beveled tip. At the low differential pressure of 3 psig, it takes several minutes for the sample to fill the capillary and detect sample 455 exiting the beveled tip. An improved alternative method to speed up filling the capillary is to increase the pressurized chamber 460 pressure to about 15 psig, which in turn fills the capillary in only about 30 seconds. When the electrospray capillary is filled, the differential pressure is reduced to 3 psig to return the flow rate to about 50 nL per min.

Positive high voltage, from a high voltage variable power supply 430, is then applied to the sample 455. The high voltage is then scanned from ~5,000 to ~5,100 volts. The Taylor cone 150 of the capillary 100 is then examined during a high voltage 430 scan to find the particular voltage at which the electrospray is stable. A stable electrospray is obtained when the Taylor cone 150 remains fixed in place and points directly away from the axis of the capillary 100, with a sharp tip and a single steady stream of material being ejected. Typically, the microscopic image of the Taylor cone appears as a 45° equilateral triangle attached to the flat tip on the end of the tapered capillary 100.

About 1.5 L per minute flow of dry gas 210 is used to introduce the droplet stream resulting from the Taylor cone 150 into the differential mobility analyzer 200 through connected tubing, after having been first charge reduced with alpha radiation source 480 to either a neutral or single positive charge state. 15 L per min of laminar excess gas flow 220 is added to the differential mobility analyzer 200. Additional dry gas 230 is introduced to collect the mobility selected particles, resulting in a mobility-classified particle flow 240 of 1.5 L per min that exits the differential mobility analyzer 200, which in turn transfers the mobility selected particles 240 to the condensation particle counter 490. By scanning the differential mobility analyzer 200 high voltage power supply 205, a data set of particles counted per second versus mobility may be created.

Additional confirmation of a stable electrospray is obtained from knowledge of the electrospray current. The TSI electrospray aerosol generator has a current meter for displaying the electrospray current output by the electrospray high voltage power supply 205. Stable electrosprays exhibit long term stability with currents varying less than ±1 nA from a typical total electrospray current of 300 nA during the course of an analysis.

Typically, an essentially pure sample of ammonium acetate buffer solution is run through the instrument to confirm that the capillary is clean. This is called a background spectrum check. Typical background spectra will indicate fewer than 7 particles per mL with particle diameters between 3-4 nm.

The software supplied with the TSI Model 3980 Gas-phase Electrophoretic-Mobility Macromolecule/nanoparticle Analysis (GEMMA) unit provides several operator defined conditions. The data recording software allows several choices for the number of size subdivisions recorded for each decade of particle diameter. Typically 64 size subdivisions per decade are recorded. The scanning range can also be selected. Typically, a scanning range of 3 nm to 100 nm is scanned for typical LDL samples; however, this range is extended to a higher limit when IDL and chylomicrons are measured, to as high as 1200 nm. Scan times are typically set to 3 min. The position of a peak in an ion mobility spectrum is determined with the manufacturer's software. Computer mouse movement is used to select the maximum value in a peak by observing a draggable indicator.

Coronary Heart Disease Risk Analysis

Differential mobility spectroscopy of lipoproteins can additionally be used for quick determinations of coronary heart disease (CHD) risk by analyzing the resultant lipoprotein size distributions.

Plasma was collected from six individuals having lipoprotein patterns previously characterized by gradient gel electrophoresis. Lipoprotein particles from these individuals were separated from plasma using ultracentrifugation to isolate components with density less than 1.20 g/cm$^3$. The lipoprotein particles were then desalted and analyzed with ion mobility spectrometry to determine the biological particle size distribution. The results for six types of lipoprotein patterns obtained by electrospray mobility spectroscopy are shown in FIG. 5.

In FIG. 5, six individual lipoprotein size spectra (510, 520, 530, 540, 550, and 560) are presented as the result of differential mobility analysis with mobilities converted to size as previously described. In all but the lowest mass value trace 560, the traces are shifted vertically in order to differentiate the graphs, which would otherwise overlap. To read the vertically shifted mass value, the trace is shifted vertically to zero mass on its lowest particle diameter. The Mass ordinate is in relatively scaled arbitrary units of grams.

Pattern A is a designation applied to individuals at relatively low risk for CHD. Pattern A lipoproteins are characterized by LDL particles larger (median size of ~22.5 nm versus ~20.8 nm) than those obtained from individuals at higher risk for coronary heart disease, i.e., Pattern B individuals. Additionally, Pattern A lipoproteins are characterized by a population of HDL particles that generally shows several subtypes. These subtypes are revealed by several peaks in the HDL region (of ~7-13 nm) for Pattern A spectra. The vertical line at approximately 8.9 nm indicates the principal HDL peak for patients with Pattern A, B, and intermediate Pattern AB. The Pattern a spectra are easily discerned by observing a second HDL peak at approximately 11 nm. With these characteristics in mind, traces 510, 520 and 530 are low risk Type A patterns. The peak in the LDL population of particles for Pattern B individuals is smaller by several nanometers than LDL particles from Pattern A individuals. The shift from pattern A to pattern B is represented approximately by the vertical lines drawn through the LDL peaks at approximately 20.8 nm (dashed), and 22.5 nm (solid). The HDL particles from Pattern B individuals, shown in traces 550 and 560, generally show less heterogeneity; here the HDL peaks for Pattern B patterns show only one sharp principal peak, as expected. Thus, the ion mobility measurements agree with gradient gel determinations and provide an alternative measurement method for assessing CHD.

Still referring to FIG. 5, trace 540 represents a patient with an intermediate Type AB pattern. This trace 540 shows an LDL peak intermediately disposed between the typical Type A peak at 22.5 nm, and the typical Type B peak of 20.8 nm. The trace 540 is also distinguished by only a single HLD peak, typical of the higher risk Type B pattern.

Ion mobility spectroscopy is quantitative and can be used to directly measure the total amount of lipoprotein particles in each of the lipoprotein classes and/or subclasses. The area under the curves, in a particle mass versus independent variable (such as size, density, mobility, etc.) distribution, is directly representative of the lipoprotein particle mass. The measurement technique relies on counting individual particles as a function of size (diameter). It is therefore possible the convert the number of particles at a specific size into a mass value using the volume and density of the particles. The density of lipoprotein particles is a well-known function of particle size and is obtainable from the literature. The mass values associated with the figure are simply scaled to indicate relative values but can be converted to actual mass of lipoproteins in plasma using dilution factors along with flow rates of sample and air passing through the ion mobility spectrometer.

The spectra in FIG. 5 also show the existence of lipoprotein particles that fall into the VLDL size class. Their presence is indicated by small bumps in the spectra above particle diameters of about 30 nm. The shaded area under the plots in this figure are proportional to particle mass and this area can be used to assess the mass of particles in any chosen particle interval such as 30 to 40 nm or 35 to 40 nm or any other choice of bin size.

Linearity Versus Density

Figure 6:
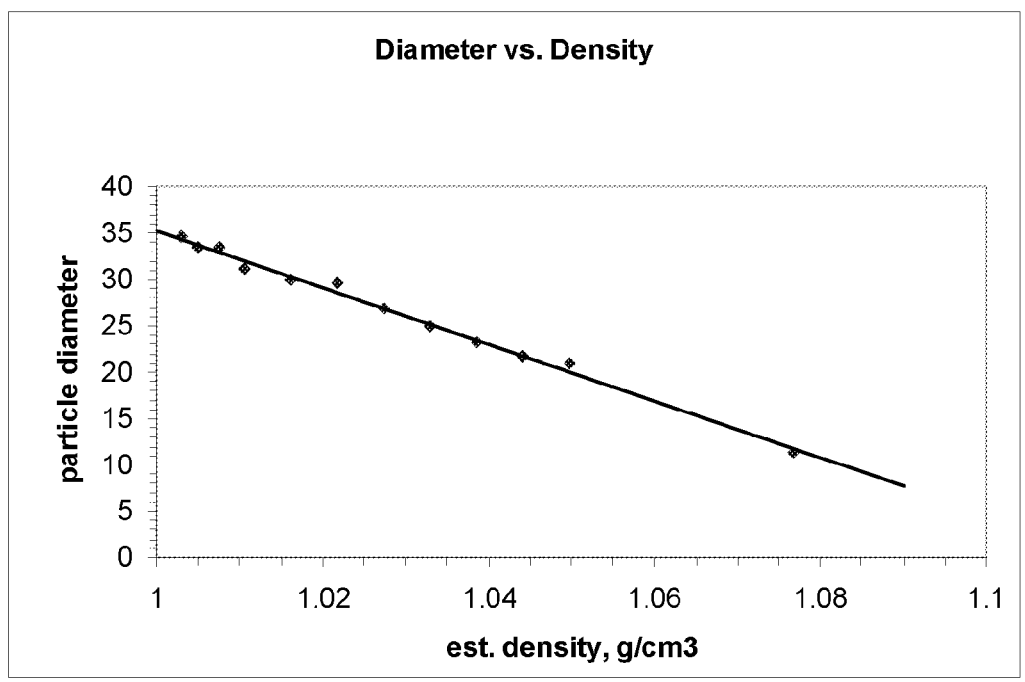
FIG. 6 is a graph indicating the approximately inverse linear relationship between lipoprotein particle diameter, and the estimated lipoprotein sample density.

A further example showing how ion mobility analysis can be implemented is shown with the data in FIG. 6. Lipoprotein particles were fractionated with non-equilibrium ultracentrifugation in NaCl/D$_2$O. The particles were removed from the ultracentrifuge tube as liquid fractions, which spanned the range of 1.0 to 1.08 g/cm$^3$. Because the ultracentrifugation step was not run until the particles reached an equilibrium flotation position in the ultracentrifuge tube the density of the lipoprotein particles removed with each fraction is only an estimate, however a reasonable estimate, of the particle's true density, and is displayed as an estimated density. FIG. 6 is a plot of lipoprotein particle diameter as a function of the solution density of each fraction reveals the expected inverse linear relationship between particle diameter and density.

FIG. 6 has an ordinate of particle diameters in nm as measured by ion mobility analysis, and an abscissa of estimated particle density in g/cm$^3$ as obtained by non-equilibrium ultracentrifugation.

In FIG. 6, the particle diameter was measured using ion mobility analysis. The results indicate, that there is an inverse linear correlation between particle diameter and particle density, as expected. Data points not exactly matching the inverse linear correlation are though to be due to the non-equilibrium floatation method used to obtain the data samples.

Linearity of Lipoprotein Mass Measurements

Figure 7:
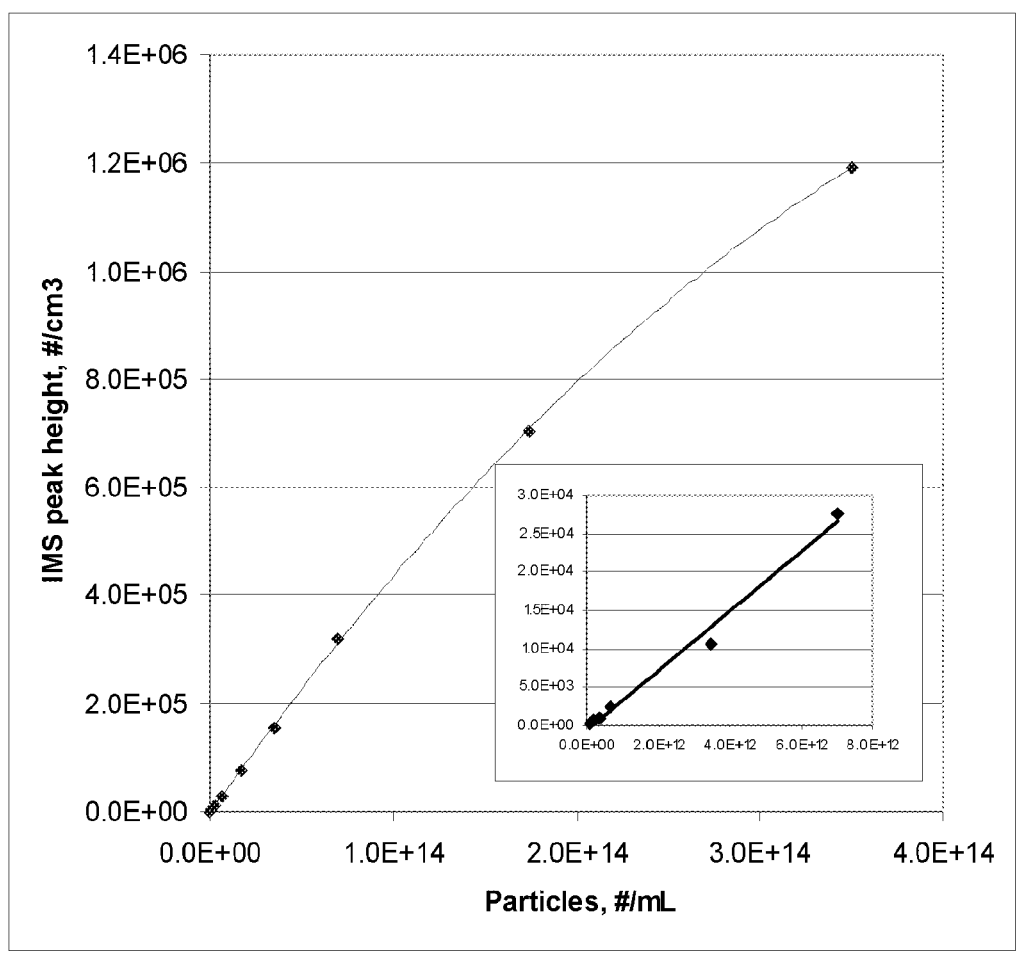
FIG. 7 is a graph indicating the approximately linear relationship between lipoprotein particle count, and the corresponding lipoprotein sample particle count.

The linearity of the detection method was verified by analyzing a series of dilutions of a specific set of LDL particles. These LDL particles were isolated by gel filtration from the other classes of lipoprotein particles. The starting concentration of these LDL particles was determined by measuring the apolipoprotein B concentration of the solution. A single molecule of apolipoprotein B is present in each LDL particle. By using the apolipoprotein B concentration it is possible to calculate the number of LDL particles in the sample. This specific sample was sequentially diluted, and the number of particles in each dilution (the IMS peak height, #/cm$^3$ axis) was determined by differential mobility spectrometry and plotted versus the calculated apolipoprotein B concentration (the Particles, #/mL axis) at each dilution. One option available with the commercial software supplied with the instrument manufactured by TSI, Inc., plots the number of particles detected per cm$^3$ of air passing through the differential mobility analyzer. Ion mobility peak height is plotted vs. the number concentration of LDL particles as determined from apolipoprotein B measurements in FIG. 7. This plot, FIG. 7, shows that the measurement is linear over more than three orders of magnitude from $10^{12}$ to $10^{14}$ particles per mL. For increased detail, the inset graph of FIG. 7 shows the range up to $8 \cdot 10^{12}$ particles per mL. FIG. 7 implies that variations in concentrations of lipoprotein subclasses will be accurately measured over a range of 1000:1, or 0.1%.

Linear Independence of Lipoprotein Analyses

Differential mobility analysis appears to be highly linearly independent over the variety of lipoprotein classes and subclasses. This linear independence was verified as shown in FIGS. 8-23. In these Figures, a single human blood sample was fractionated into 16 different average densities. The method used was non-equilibrium ultracentrifugation. One byproduct of this type of fractionation is that there is always a distribution of densities about an average density. Since we are dealing with biological particles, there are wide ranges of sizes comprising in the fractions having a particular average densities. An attempt was made to select density fractions representing each of the lipoprotein particle subclasses.

FIGS. 8-23 show resultant differential mobility analysis scans of 16 fractions of human lipoprotein over a range of selected average densities spanning the various human lipoprotein classes and subclasses. Lipoprotein particles were prepared as above from human plasma, then subjected to ultracentrifugation. A density gradient in an ultracentrifuge tube was prepared with NaCl dissolved in D$_2$O. The choice of gradient composition provided a way to separate lipoprotein particles with average densities varying between about 1.000 (FIG. 8) and 1.090 g/cm$^3$ (FIG. 23) from other material in the plasma. For reference purposes, gel electrophoresis gradient 8 is used to separate average densities over a range from about 1.000 (FIG. 8) to 1.062 g/cm$^3$ (bracketed between FIGS. 19 and 20). This density gradient distributes lipoprotein particles along the length of the ultracentrifuge tube. Lipoproteins with higher density such as HDL move to the bottom of the ultracentrifuge tube, as do protein molecules. Lower density lipoproteins such as VLDL rise to the top of the tube during the ultracentrifugation process.

The resulting liquid in the ultracentrifuge tube was distributed into 16 fractions, which were subsequently dialyzed against 25 mM ammonium acetate for 3 hours using a 10,000 molecular weight cut-off dialysis membrane.

The size distribution of the lipoprotein particles in each fraction was then determined using ion mobility spectral analysis. These size distributions appear in FIGS. 8-23, and have densities that correspond to lipoprotein classes and subclasses as indicated in VLDL I (FIGS. 8-10) and II (FIG. 11), IDL I (FIG. 12) and II (FIG. 13), and LDL I (FIG. 14), IIa (FIG. 15), IIb (FIG. 16), IIIa (FIG. 17), IVa (FIGS. 18 and 19), and HDL IIa (FIGS. 20-23). The fractions of FIGS. 8-23, and their subsequent density analyses, are somewhat confusing since the original laboratory sample labels of fractions are respectively 1*a*, 1*b*, 2*a*, 2*b*, 3-10, 11*a*, 11*b*, 12*a*, and 12*b*. Consequently, the sample labels bear some resemblance to the lipoprotein subclasses. Lipoprotein subclass 111*b* was not shown in this selection of fractions, although based on the complement of FIGS. 8-23, the IIIb distribution should be similarly peaked within a range of 1.041 and 1.044 g/cm$^3$ as indicated on FIG. 2. Each particle size distribution is plotted as mass vs. particle diameter. In each Figure, the mass value refers to the mass of particles per m$^3$ at each indicated particle diameter where m$^3$ is referenced to the volume of lipoprotein-laden gas entering the differential mobility analyzer. Although only single positively charged particles are measured due to the selective electromotive classification used by the DMA, the μg/m$^3$ number is corrected for the fraction of particles that are charged in any given particle size interval. This rate does not take into account either the rate at which a sample solution is electrosprayed, or the flow rate of flow gas that sweeps the particles towards the DMA. This mass value can be converted into the mass of lipoprotein particles present in the original sample plasma by using the information of the gas flow rate, flow rate of electrosprayed sample, particle transfer efficiency and liquid dilution factors.

FIGS. 9-18, 20, 21, and 23 indicate that for lipoprotein densities ranging from about 1.003-1.090 g/cm$^3$, in this particular human sample, each density sample through ultracentrifugation results in one principal peak in the mass versus size graph.

Figure 8:
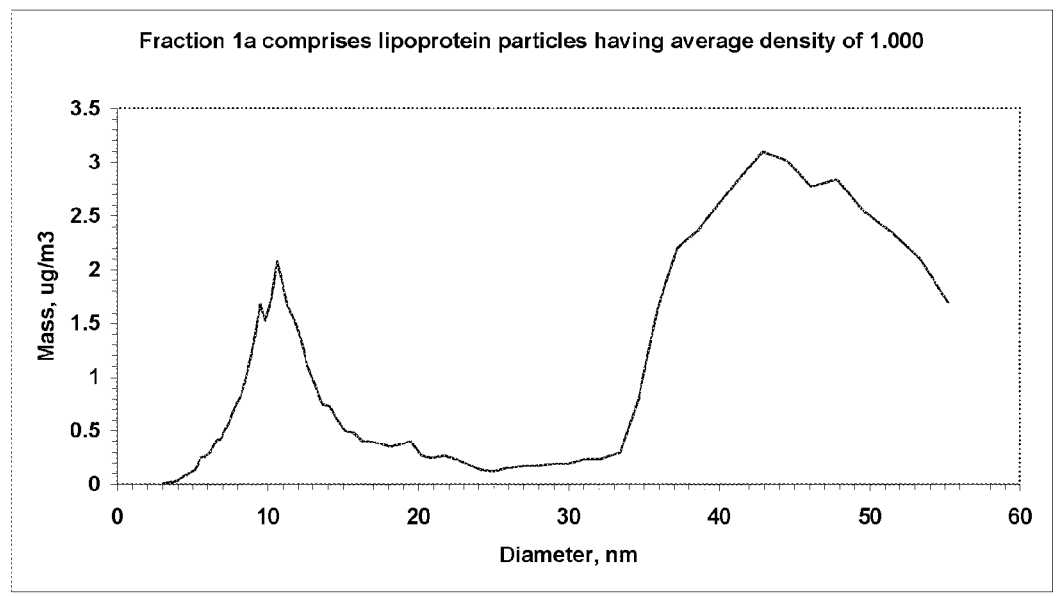
FIG. 8 is a differential mobility spectral scan of a sample of lipoprotein having an average density of about 1.000 g/cm$^3$, corresponding to VLDL I.
Figure 9:
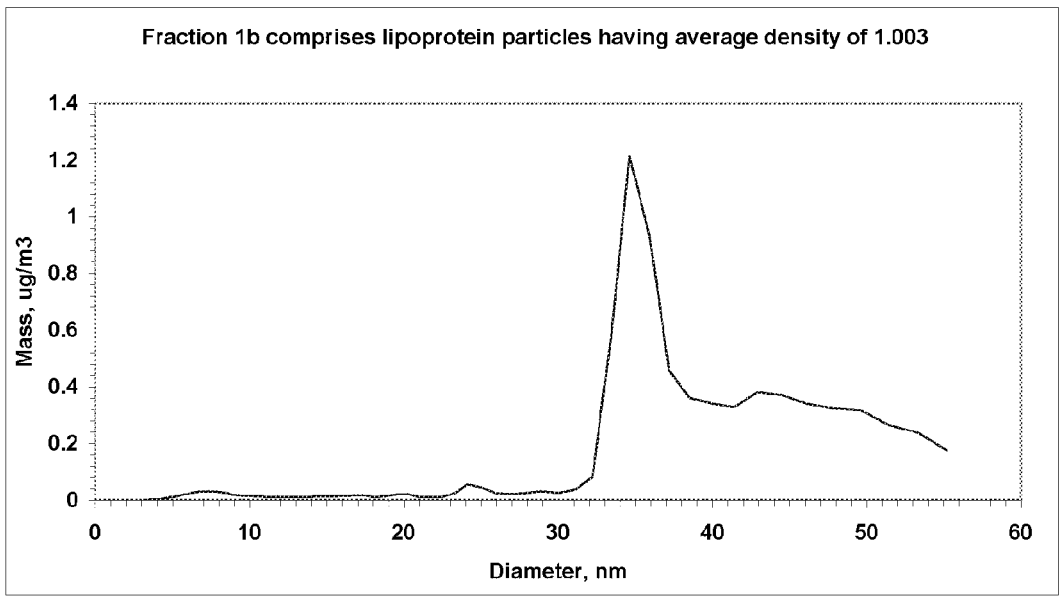
FIG. 9 is a differential mobility spectral scan of a sample of lipoprotein having an average density of about 1.003 g/cm$^3$, corresponding to VLDL I.
Figure 10:
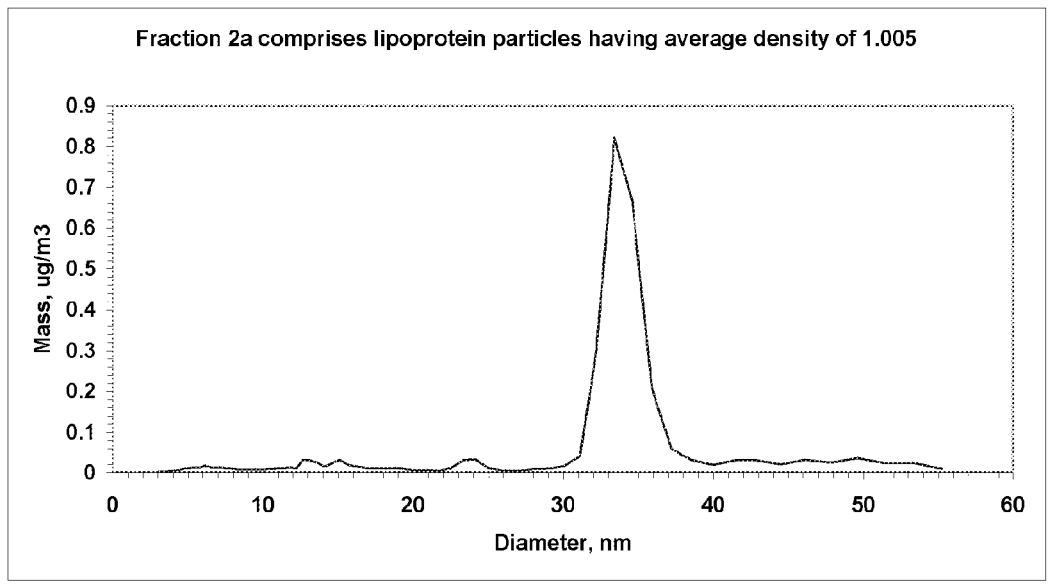
FIG. 10 is a differential mobility spectral scan of a sample of lipoprotein having an average density of about 1.005 g/cm$^3$, corresponding to VLDL I.
Figure 11:
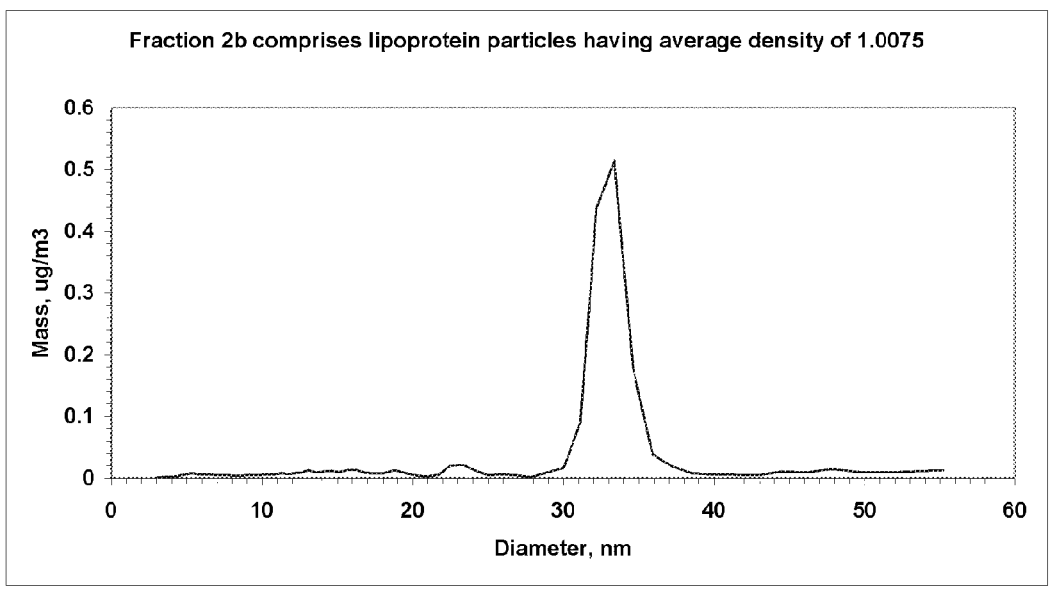
FIG. 11 is a differential mobility spectral scan of a sample of lipoprotein having an average density of about 1.0075 g/cm$^3$, corresponding to VLDL II.
Figure 12:
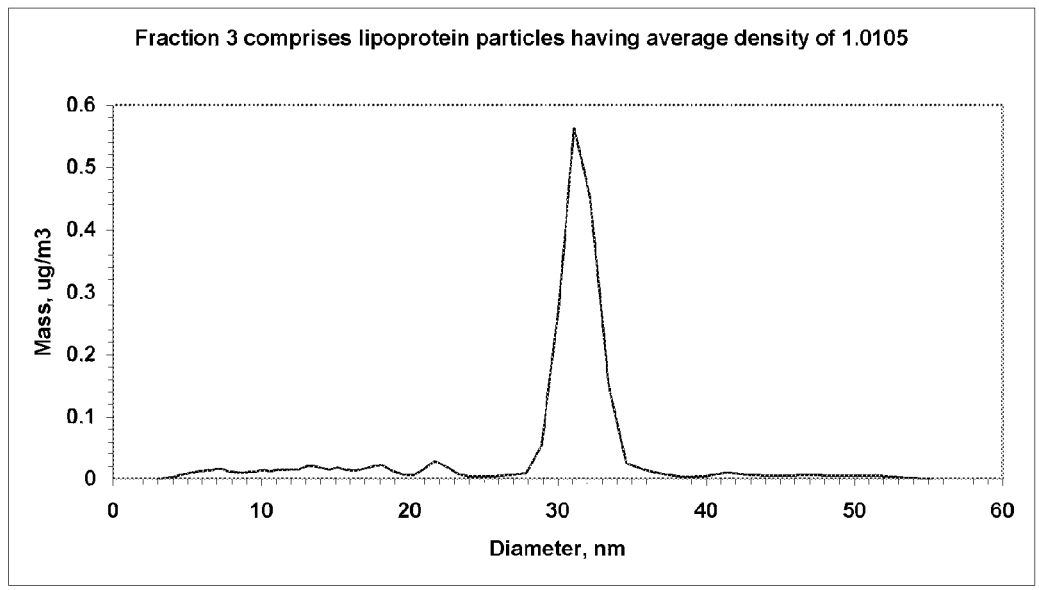
FIG. 12 is a differential mobility spectral scan of a sample of lipoprotein having an average density of about 1.0105 g/cm$^3$, corresponding to IDL I.
Figure 13:
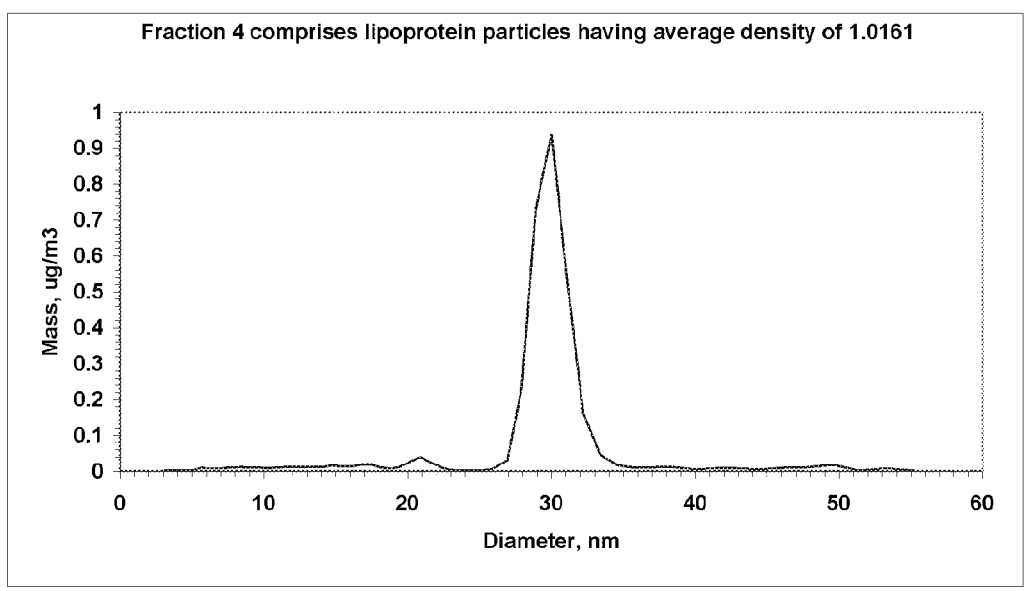
FIG. 13 is a differential mobility spectral scan of a sample of lipoprotein having an average density of about 1.0161 g/cm$^3$, corresponding to IDL II.
Figure 14:
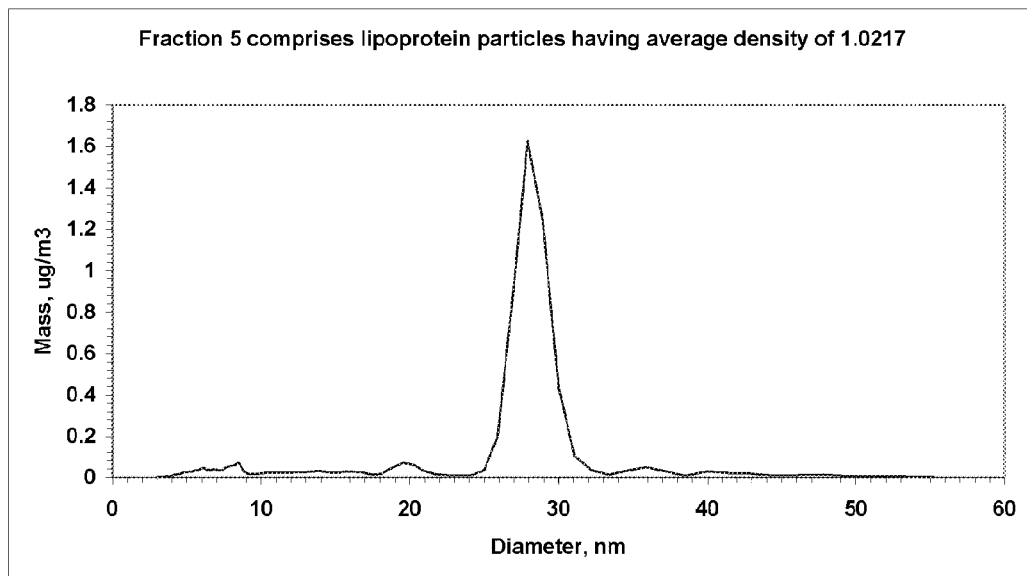
FIG. 14 is a differential mobility spectral scan of a sample of lipoprotein having an average density of about 1.0217 g/cm$^3$, corresponding to LDL I.
Figure 15:
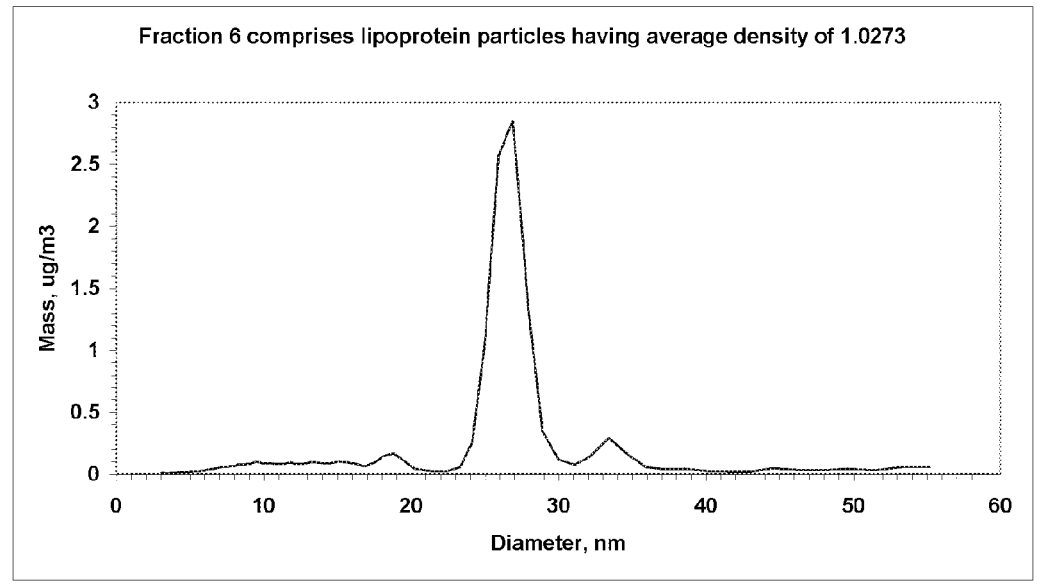
FIG. 15 is a differential mobility spectral scan of a sample of lipoprotein having an average density of about 1.0273 g/cm$^3$, corresponding to LDL IIa.
Figure 16:
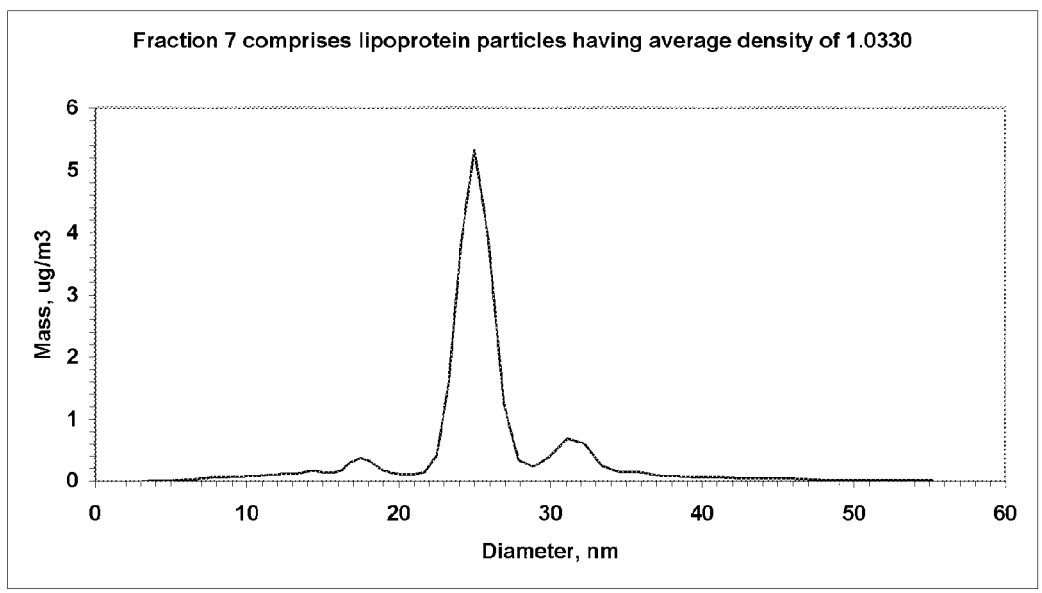
FIG. 16 is a differential mobility spectral scan of a sample of lipoprotein having an average density of about 1.0330 g/cm$^3$, corresponding to LDL IIb.
Figure 17:
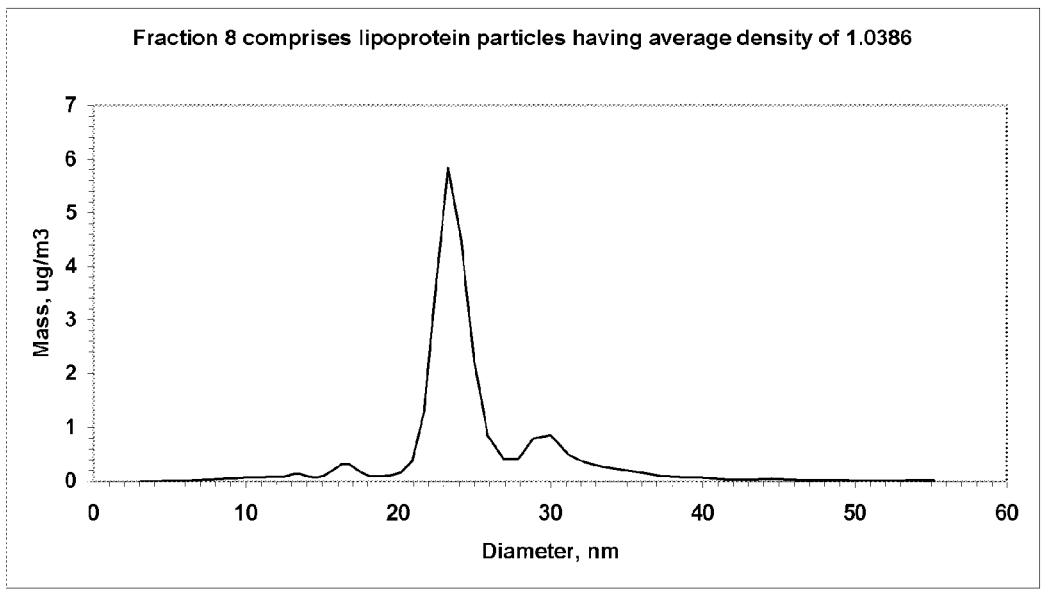
FIG. 17 is a differential mobility spectral scan of a sample of lipoprotein having an average density of about 1.0386 g/cm$^3$, corresponding to LDL
Figure 18:
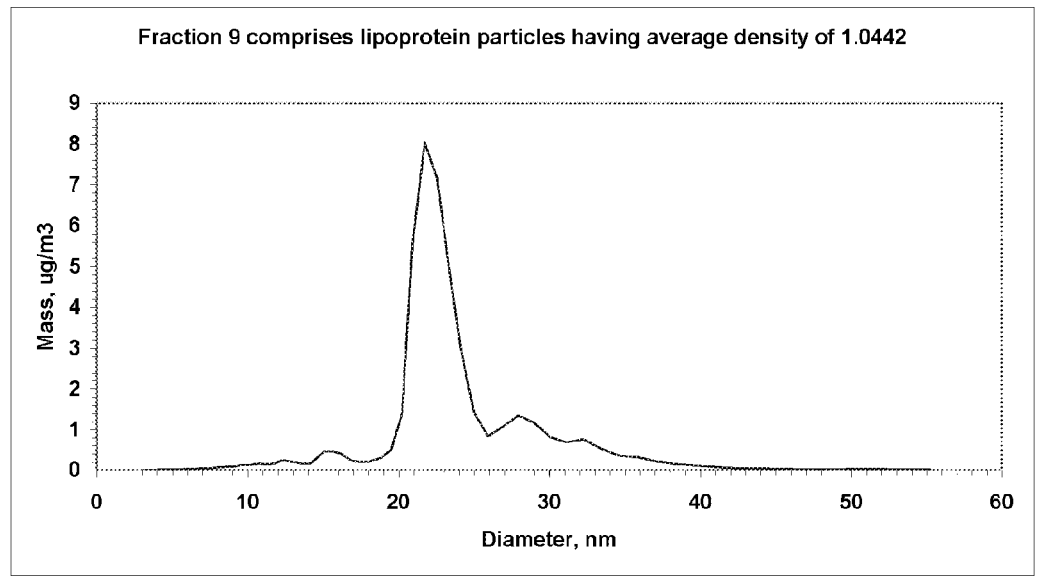
FIG. 18 is a differential mobility spectral scan of a sample of lipoprotein having an average density of about 1.0442 g/cm$^3$, corresponding to LDL IVa.
Figure 19:
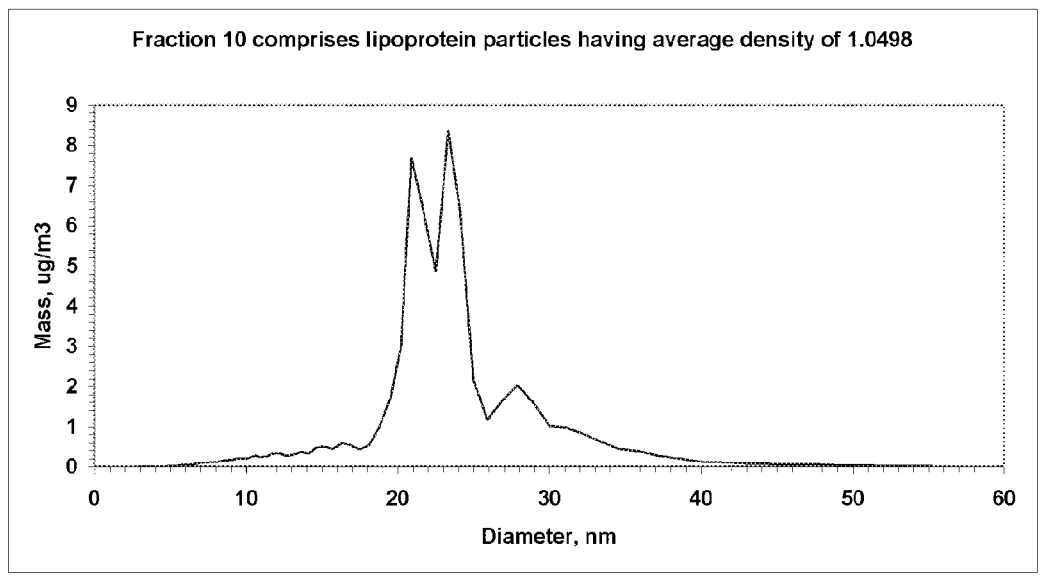
FIG. 19 is a differential mobility spectral scan of a sample of lipoprotein having an average density of about 1.0498 g/cm$^3$, corresponding to LDL IVa.
Figure 20:
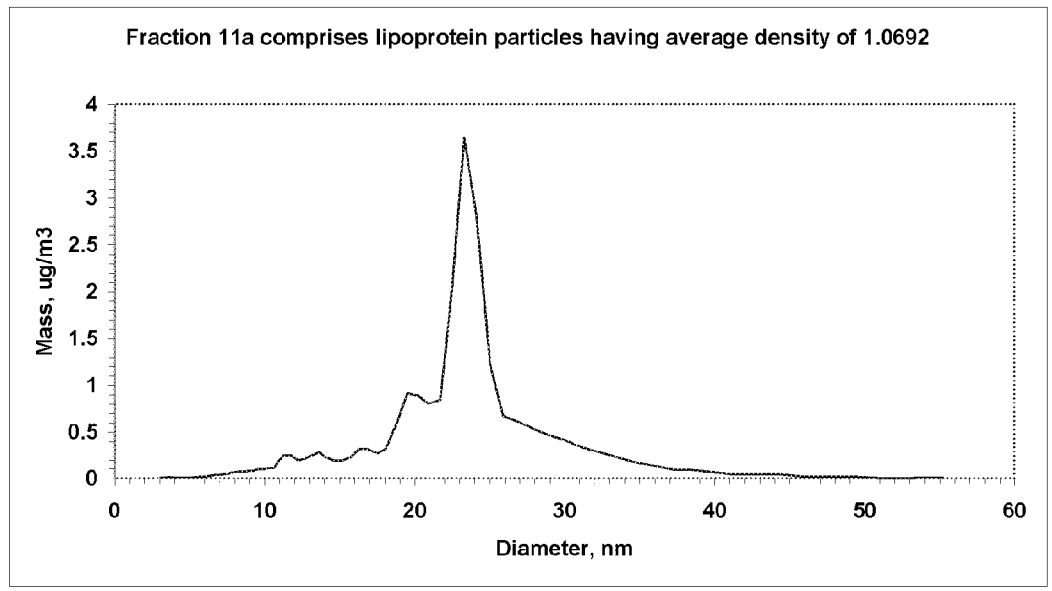
FIG. 20 is a differential mobility spectral scan of a sample of lipoprotein having an average density of about 1.0692 g/cm$^3$, corresponding to HDL IIb.
Figure 21:
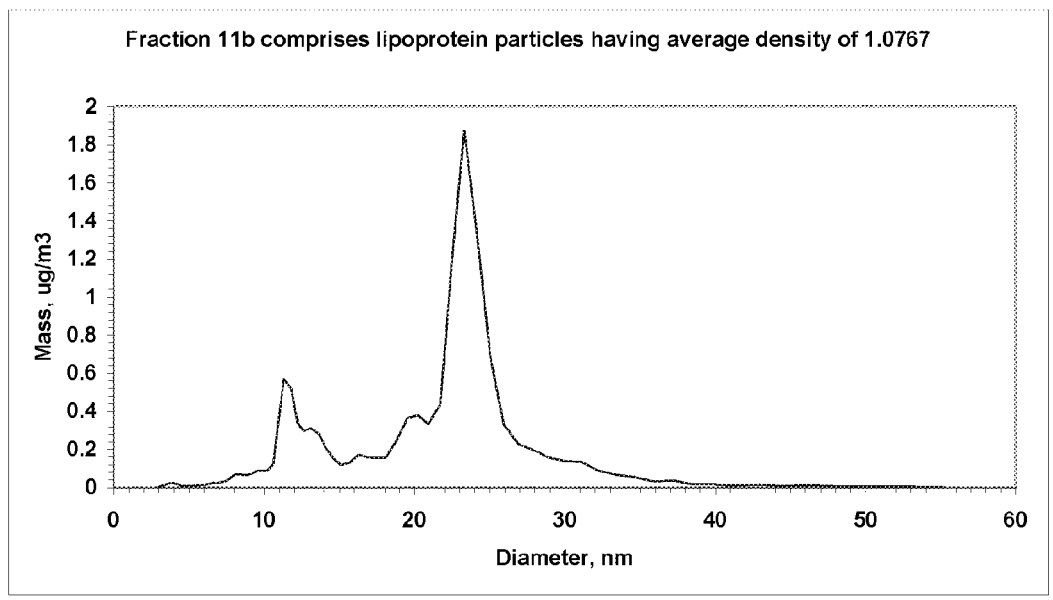
FIG. 21 is a differential mobility spectral scan of a sample of lipoprotein having an average density of about 1.0767 g/cm$^3$, corresponding to HDL IIb.
Figure 22:
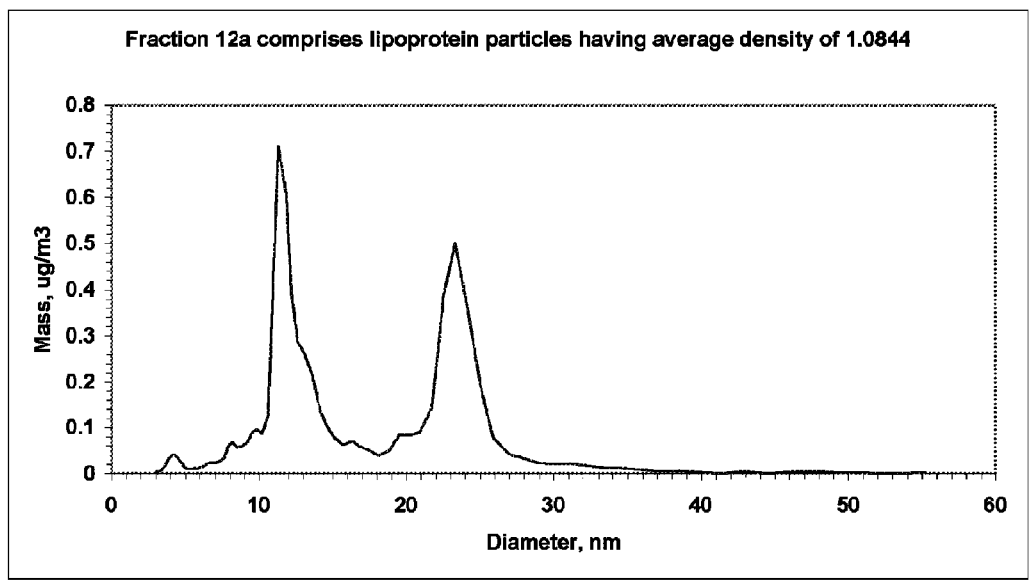
FIG. 22 is a differential mobility spectral scan of a sample of lipoprotein having an average density of about 1.0844 g/cm$^3$, corresponding to HDL IIb.
Figure 23:
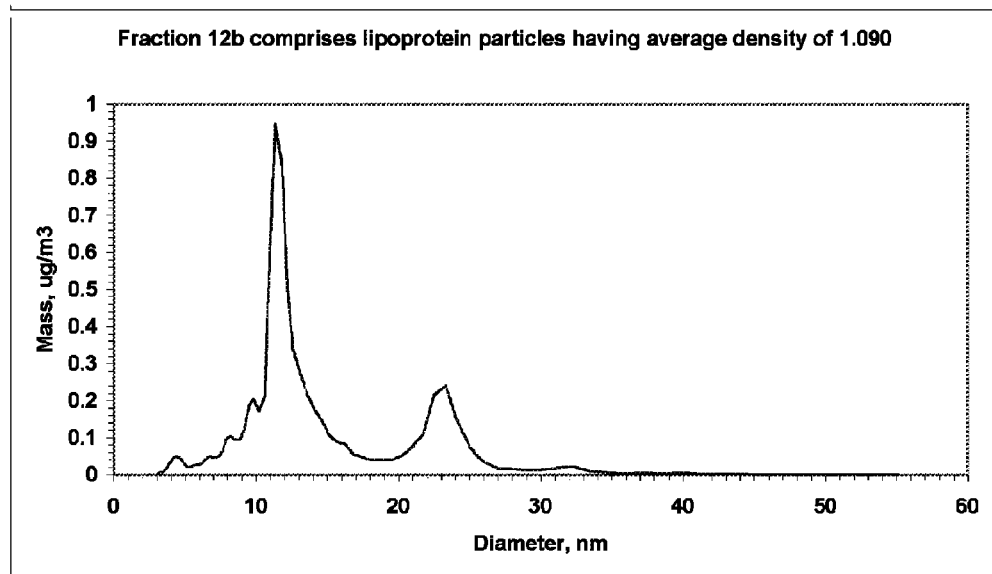
FIG. 23 is a differential mobility spectral scan of a sample of lipoprotein having an average density of about 1.090 g/cm$^3$, corresponding to HDL IIb.

For FIGS. 8, 19, and 22 there is some bimodality and broadening of the peaks. It is not presently understood what these broadened and bimodal lipoprotein distributions represent. It is possible that this bimodality could be an artifact of the sample preparation method discusses above. That is, the sample preparation technique could be disruptive enough to break apart some of the agglomerated biological particles, resulting in smaller sized fragments. If this is the case, then a modification of the sample preparation method could then resolve these samples into relatively clean single peak size spectra as well.

The bimodality and broadening could also be an artifact resulting from the nonequilibrium ultracentrifugation used to generate the subfractions in this particular experiment. This issue will be resolved by further experiment.

Nonequilibrium ultracentrifugation also results in the non-steady state densities determined in FIGS. 8-23. As such, all densities in these FIGS. 8-23 are approximate.

Linear Superposition of Lipoprotein Subclasses

In principal, for lipoproteins represented in these subclasses, an entire plasma sample could be mathematically represented by the linear superposition of each lipoprotein subclass. Even if, ultimately, the multiple peak phenomenon remains, then traditional numerical methods of data correlation such as least squares or singular value decomposition could be used to determine the amount of each lipoprotein subclass in an entire sample. Thus, in a single differential mobility spectral scan, the quantity of each lipoprotein subclass a plasma sample could be determined. After making this determination, both the quantity and type of each lipoprotein would be known. By statistically correlating the resulting subclass information with population mortality and risk factors, a more accurate assessment of coronary heart disease risk would result. In particular, the known characteristics of a bimodal vs. unimodal HDL distribution, and the peak lipoprotein diameter of the LDL distribution, could be readily transformed into a risk factor ranging from 100% Type A pattern (low risk) to 100% Type B pattern (high risk).

CONCLUSION

All publications, patents, and patent applications mentioned in this specification are herein incorporated by reference to the same extent as if each individual publication or patent application were each specifically and individually indicated to be incorporated by reference.

The description given here, and best modes of operation of the invention, are not intended to limit the scope of the invention. Many modifications, alternative constructions, and equivalents may be employed without departing from the scope and spirit of the invention.

What is claimed is:

1. A method for assessing a lipid-related health risk in a patient, the method comprising:
    (a) isolating lipoprotein particles from a biological sample taken from a patient suspected of having a lipid-related health risk;
    (b) delivering the lipoprotein particles in a charged state to a differential mobility analyzer;
    (c) obtaining a mobility distribution of the charged lipoprotein particles;
    (d) comparing the mobility distribution of the charged lipoprotein particles from the patient to a reference lipoprotein particle mobility distribution; and
    (e) determining whether the patient has the lipid-related health risk based on the comparison.

2. The method of claim 1, wherein the lipoprotein particles are put into a charged state by electrospraying the lipoprotein particles.

3. The method of claim 1, wherein the lipoprotein particles comprise at least one lipoprotein selected from the group consisting of VLDL, IDL, LDL, HDL, and their subclasses.

4. The method of claim 1, wherein the biological sample is blood, plasma or serum.

5. The method of claim 1, wherein the lipoprotein particles from the patient are classified on the basis of the mobility distribution.

6. The method of claim 1, further comprising converting the mobility distribution of lipoprotein particles to at least one measurement selected from the group consisting of a particle mobility, a particle size, a particle density, a particle mass, a number of particles in a size interval, and an amount of particle mass in a size interval, prior to determining the lipid-related health risk of the patient.

7. The method of claim 1, wherein the lipid-related health risk is hyperlipidemia.

8. The method of claim 7, wherein the hyperlipidemia is hypertriglyceremia.

9. The method of claim 1, wherein the lipid-related health risk is the risk for a cardiovascular condition or disease, or the risk for a predisposition to develop a cardiovascular condition or disease.

10. The method of claim 9, wherein the cardiovascular disease is coronary heart disease.

11. A method for determining a lipid-related health risk in a patient, the method comprising:
    (a) obtaining lipoprotein particles from a patient sample, wherein the patient is suspected of having a lipid-related health risk;
    (b) delivering lipoprotein particles in a charged state to a differential mobility analyzer;
    (c) obtaining a mobility distribution of the charged lipoprotein particles;
    (d) comparing the mobility distribution of the charged lipoprotein particles from the patient to a reference lipoprotein particle mobility distribution taken from a patient that does not have the lipid-related health risk; and
    (e) determining whether the patient has the lipid-related health risk based on the comparison.

12. The method of claim 11, wherein the charged lipoprotein particles comprise at least one lipoprotein selected from the group consisting of VLDL, IDL, LDL, HDL, and their subclasses.

13. The method of claim 11, wherein the patient sample is blood, plasma or serum.

14. The method of claim 11, wherein the charged lipoprotein particles from the patient are classified on the basis of the mobility distribution.

15. The method of claim 11, further comprising converting the mobility distribution of lipoprotein particles to at least one measurement selected from the group consisting of a particle mobility, a particle size, a particle density, a particle mass, a number of particles in a size interval, and an amount of particle mass in a size interval, prior to determining the lipid related health risk of the patient.

16. The method of claim 11, wherein the lipid-related health risk is hyperlipidemia.

17. The method of claim 16, wherein the hyperlipidemia is hypertriglyceremia.

18. The method of claim 11, wherein the lipid-related health risk is the risk for a cardiovascular condition or disease, or the risk for a predisposition to develop a cardiovascular condition or disease.

19. The method of claim 18, wherein the cardiovascular disease is coronary heart disease.

20. The method of claim 11, wherein the lipoprotein particles are put into a charged state by electrospraying the lipoprotein particles.

* * * * *